United States Patent [19]

Wade

[11] Patent Number: 5,089,493
[45] Date of Patent: Feb. 18, 1992

[54] TRIAZOLO(1,5-C)PYRIMIDO(1,4)AZINES AS BRONCHODILATORS

[75] Inventor: James J. Wade, Oakdale, Minn.

[73] Assignee: Riker Laboratories, Inc., St. Paul, Minn.

[21] Appl. No.: 610,556

[22] Filed: Nov. 8, 1990

Related U.S. Application Data

[60] Division of Ser. No. 296,713, Jan. 17, 1989, Pat. No. 4,981,850, which is a continuation-in-part of Ser. No. 152,443, Feb. 5, 1988, abandoned.

[51] Int. Cl.$^5$ ............................................. C07D 498/02
[52] U.S. Cl. ................................. 514/229.8; 544/101
[58] Field of Search ....................... 544/101; 514/229.8

[56] References Cited

U.S. PATENT DOCUMENTS

| | | | |
|---|---|---|---|
| 4,134,974 | 1/1979 | Melloni et al. | 544/101 |
| 4,477,450 | 10/1984 | Wade | 544/263 |
| 4,503,050 | 3/1985 | Wade | 514/222 |
| 4,547,499 | 10/1985 | Hester | 544/101 |
| 4,572,910 | 2/1986 | Wade | 544/263 |
| 4,639,445 | 1/1987 | McQuinn et al. | 514/228.5 |
| 4,734,413 | 3/1988 | Wade | 514/222 |
| 4,738,175 | 5/1988 | Kasztrelner et al. | 544/105 |

OTHER PUBLICATIONS

Sazonov et al., Khimiya Geterotsiklicheskikh, 1973, 171.
Sazonov et al., Khimiya Geterotsiklicheskikh, 1972, 1285.
Sazonov et al., Khimiya Geterotsiklicheskikh, 1976, 681.
Melik-Ogandzhanyan et al., Khimiya Geterotsiklicheskikh Soedinenii, 1985, 974.
E. F. Schroeder and R. M. Dodson, J. Amer. Chem. Soc., 84, 1904–1913 (1962).
R. N.. Henri, R. A. Lazarus and S. J. Benkovic, J. Med. Chem., 26, 559–563 (1983).
Aust. J. Chem. 1981, 34, 189 (Brown et al.).

Primary Examiner—Donald G. Daus
Attorney, Agent, or Firm—Gary L. Griswold; Walter N. Kirn; Douglas E. Reedich

[57] ABSTRACT

Substituted 1,2,4-triazolo[1,5-c]pyrimido[1,4]-azines have been found to have potent bronchodilator activity. Pharmacological methods for inducing bronchodilation using such compounds, pharmaceutical compositions containing such compounds, and synthetic intermediates for preparing such compounds are also described.

19 Claims, No Drawings

TRIAZOLO(1,5-C)PYRIMIDO(1,4)AZINES AS BRONCHODILATORS

CROSS-REFERENCE TO RELATED APPLICATION

This application is a division of Ser. No. 296,713, which was filed Jan. 17, 1989, now U.S. Pat. No. 4,981,850, which is a continuation-in-part of copending U.S. Ser. No. 152,443, which was filed on Feb. 5, 1988 now abandoned.

TECHNICAL FIELD

This invention relates to novel heterocyclic compounds exhibiting bronchodilator activity. Pharmacological methods of using such compounds, pharmaceutical formulations containing such compounds and synthetic intermediates for preparing such compounds are also described.

BACKGROUND OF THE INVENTION

A variety of aromatic heterocyclic compounds are known to exhibit bronchodilator activity. One of the most widely used compounds for treatment of mammals is theophylline, which has the structure shown below:

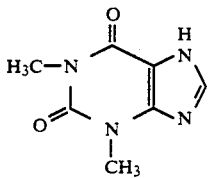

Numerous attempts to obtain a safer, more potent bronchodilator have not yet supplanted theophylline.

Pyrimido[5,4-b]oxazines are known compounds which are reported by Sazonov, et al., Khimiya Geterotsiklicheskikh Soedinenii, 1973, 171; ibid., 1972, 1285, and ibid., 1976, 681. These compounds, which have not been described as bronchodilators, have the following structure:

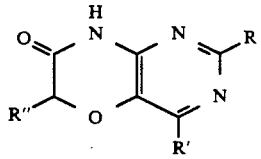

wherein R is amino, acetamido, hydrogen or methyl; R' is hydrogen, methyl, hydrazino, piperidino, morpholino, methoxy, methylthio, mercapto, chloro or hydroxy; and R" is hydrogen, methyl, ethyl, propyl, or dimethyl.

Pyrimido[4,5-b][1,4]oxazines are known compounds which are reported by Melik-Ogandzhanyan, et al., Khimiya Geterotsiklicheskikh Soedinenii, 1985, 974. The corresponding 4-chloro, 4-hydroxy, 4-dialkylamino, 4-morpholino and 4-piperidino derivatives are reported. They have the following structure:

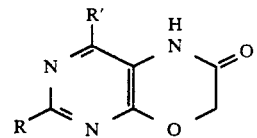

wherein R is methyl or hydrogen and R' is chloro, hydroxy, N,N-dimethylamino, N,N-diethylamino, morpholino or piperidino. None of the reported compounds were described as bronchodilators.

Some pyrimido[5,4-b][1,4]thiazines are known, reported by E. F. Schroeder and R. M. Dodson, J. Amer. Chem. Soc., 84, 1904-1913 (1962) and by R. N. Henri, R. A. Lazarus and S. J. Benkovic, J. Med. Chem., 26, 559-563 (1983). None of the reported compounds were described as bronchodilators.

U.S. Pat. Nos. 4,477,450 and 4,572,910, respectively, disclose triazolo[4,3-c]pyrimidines and triazolo[1,5-c]pyrimidines which contain a heterocyclic amine moiety such as piperazino, piperidino, morpholino or thiomorpholino on the 5 and/or 7-position of the pyrimidine ring. These compounds are bronchodilators.

Triazolo[1,5-c]pyrimido[4,5-b][1,4]oxazines, triazolo[1,5-c]pyrimido[5,4-b][1,4]oxazines and triazolo[1,5-c]pyrimido[5,4 b][1,4]thiazines have not previously been reported.

DETAILED DESCRIPTION OF THE INVENTION

The present invention relates to substituted 1,2,4-triazolo[1,5-c]pyrimido[1,4]azines which are bronchodilators. The invention also relates to a method for obtaining bronchodilation in a mammal using a 1,2,4-triazolo[1,5 c]pyrimido[1,4]azine of the invention, and to pharmaceutical compositions comprising an effective amount of a 1,2,4-triazolo[1,5-c]pyrimido[1,4]azine of the invention and a pharmaceutically acceptable carrier. The invention also relates to synthetic intermediates useful for preparing pharmaceutical compounds of the invention.

More specifically, the present invention relates to compounds of Formula I below

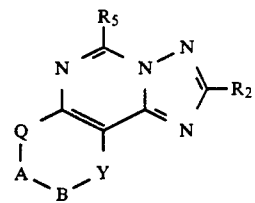

wherein A is methylene or carbonyl; B is methylene, carbonyl or —CHR$_9$—; Q is N—R$_7$ or O, with the proviso that when Q is O then A is methylene and B is methylene or carbonyl; Y is N—R$_{10}$, O, S, SO or SO$_2$, with the provisos that when Y is N—R$_{10}$, Q is O, when Q is N—R$_7$, Y is not N—R$_{10}$ and B is not carbonyl, and when Q is O, Y is N—R$_{10}$; R$_2$ is hydrogen or lower alkyl; R$_5$ is lower alkyl; R$_7$ is hydrogen, lower alkyl, benzyl or acetyl, with the proviso that when R$_7$ is hydrogen or acetyl and Y is S, SO or SO$_2$, then A is methylene; R$_9$ is lower alkyl; and R$_{10}$ is lower alkyl or benzyl; and pharmaceutically acceptable acid addition salts of compounds wherein A is methylene and B is methylene or —CHR$_9$—. Three subsets of Formula I are described herein below: compounds of Formula VI wherein Y is O and Q is NR$_7$, compounds of Formula VI wherein Y is N—R$_{10}$ and Q is O, and compounds of Formula XIX and Formula XXVI wherein Y is shown as S, but could also be oxidized to SO or SO$_2$.

The instant invention also provides novel compounds of Formula II below

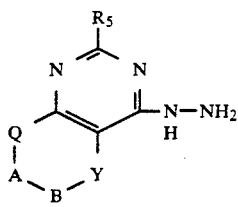

wherein A is methylene or carbonyl; B is methylene, carbonyl or —CHR$_9$—; Q is N—R$_7$ or O, with the proviso that when Q is O, then A is methylene and B is methylene or carbonyl; Y is N—R$_{10}$, O, S, SO or SO$_2$, with the provisos that when Y is N—R$_{10}$, Q is O, when Q is N—R$_7$, Y is not N—R$_{10}$ and B is not carbonyl, and when Q is O, Y is N—R$_{10}$; R$_5$ is lower alkyl; R$_7$ is hydrogen, lower alkyl or benzyl, with the proviso that when R$_7$ is hydrogen and Y is S, SO or SO$_2$, then A is methylene; R$_9$ is lower alkyl; and R$_{10}$ is lower alkyl or benzyl. The compounds of Formula II are useful intermediates for preparing compounds of Formula I.

Also, the instant invention further provides compounds of Formula III below

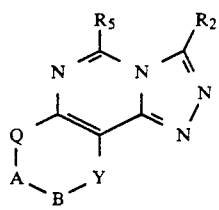

wherein A is methylene or carbonyl; B is methylene, carbonyl or —CHR$_9$—; Q is N—R$_7$ or O, with the proviso that when Q is O, then A is methylene and B is methylene or carbonyl; Y is N—R$_{10}$, O, S, SO or SO$_2$ with the provisos that when Y is N—R$_{10}$, Q is O, when Q is N—R$_7$, Y is not N—R$_{10}$ and B is not carbonyl, and when Q is O, Y is N—R$_{10}$; R$_2$ is hydrogen or lower alkyl; R$_5$ is lower alkyl; R$_7$ is hydrogen, lower alkyl, benzyl or acetyl, with the proviso that when R$_7$ is hydrogen or acetyl and Y is S, SO or SO$_2$, then A is methylene; R$_9$ is lower alkyl; and R$_{10}$ is lower alkyl or benzyl. The compounds of Formula III are also useful intermediates for preparing compounds of Formula I.

"Lower alkyl" as used in the instant specification and claims designates straight and branched-chain alkyl groups containing one to about 4 carbon atoms. Preferred lower alkyl groups are methyl and ethyl.

The presently preferred compounds of the invention are listed below. These compounds are preferred because of their generally higher potency in protecting against histamine-induced contraction of isolated guinea pig tracheal tissue. This assay is discussed in greater detail below.

Specific examples of preferred compounds which are active in the aforementioned assay at concentrations of 5 micrograms per milliliter or lower are:

8,9-dihydro-2 ethyl-5-methyl-7H-1,2,4-triazolo[1,5-c]pyrimido[5,4-b][1,4]oxazin-8-one,
8,9-dihydro-2,5,7-triethyl-1,2,4-triazolo[1,5-c]pyrimido[5,4-b][1,4]oxazin-8-one hydrate,
2,5-diethyl-8,9-dihydro-7-methyl-1,2,4-triazolo[1,5-c]pyrimido[5,4-b][1,4]thiazin-8-one,
7-(n-butyl)-2,5-diethyl-8,9-dihydro-1,2,4-triazolo[1,5-c]pyrimido[5,4-b][1,4]thiazin-8-one
7-benzyl-8,9-dihydro-2,5,9-triethyl-1,2,4-triazolo[1,5-c]pyrimido[5,4-b][1,4]thiazin-8-one,
8,9-dihydro-5-ethyl-2-methyl-7H-1,2,4-triazolo[1,5-c]pyrimido[5,4-b][1,4]thiazine,
7-benzyl-8,9-dihydro-5-ethyl-2-methyl-1,2,4-triazolo[1,5-c]pyrimido[5,4-b][1,4]thiazine,
5,7-diethyl-8,9-dihydro-2-methyl-1,2,4-triazolo[1,5-c]pyrimido[5,4-b][1,4]thiazine,
7-benzyl-2,5-diethyl-8,9-dihydro-1,2,4-triazolo[1,5-c]pyrimido[5,4-b][1,4]thiazine,
8,9-dihydro-2-ethyl-5-methyl-7H-1,2,4-triazolo[1,5-c]pyrimido[5,4-b][1,4]oxazine,
2,5-diethyl-8,9-dihydro-7H-1,2,4-triazolo[1,5-c]pyrimido [5,4-b][1,4]oxazin-8-one,
2,9-diethyl-8,9-dihydro-7H-5-methyl-1,2,4-triazolo[1,5-c]pyrimido[5,4-b][1,4]oxazin-8-one,
8,9-dihydro-5,9-dimethyl-2-ethyl-7H-1,2,4-triazolo[1,5-c]pyrimido[5,4-b][1,4]oxazin-8 one,
8,9-dihydro-2,5,9-trimethyl-7H-1,2,4-triazolo[1,5-c]pyrimido[5,4-b][1,4]oxazin-8-one,
8,9-dihydro-2,5,9-triethyl-7H-1,2,4-triazolo[1,5-c]pyrimido[5,4-b][1,4]oxazin-8-one,
5,9-diethyl-8,9-dihydro-2-methyl-7H-1,2,4-triazolo[1,5-c]pyrimido[5,4-b][1,4]oxazin-8-one,
2,5-diethyl-8,9-dihydro-9-methyl-7H-1,2,4-triazolo[1,5-c]pyrimido[5,4-b][1,4]oxazin-8-one,
7-(n-butyl)-8,9-dihydro 5-ethyl-2-methyl-1,2,4-triazolo[1,5-c]pyrimido[5,4-b][1,4]thiazin-8-one,
2,7-diethyl-8,9-dihydro-5-methyl-1,2,4-triazolo[1,5-c]pyrimido[5,4-b][1,4]thiazine,
2,5-diethyl-8,9-dihydro-7H-1,2,4-triazolo[1,5-c]pyrimido[5,4-b][1,4]thiazine,
2,5-diethyl-8,9-dihydro-7-methyl-1,2,4-triazolo[1,5-c]pyrimido[5,4-b][1,4]thiazine,
2,5-diethyl-8,9-dihydro-10-methyl-1,2,4-triazolo[1,5-c]pyrimido[4,5-b][1,4]oxazine, and
8,9-dihydro-2,5,10-triethyl-1,2,4-triazolo[1,5-c]pyrimido[4,5-b][1,4]oxazine.

Particularly preferred compounds of Formula I are the last fourteen mentioned above.

Compounds of Formula I are bronchodilators. The bronchodilator activity of the compounds of Formula I may be shown by the measurement of effects on isolated tracheal spirals. This is a well-known and long established in vitro test method. The bronchodilator activity is determined according to the following procedure: Female guinea pigs were sacrificed and each trachea removed and cut into a spiral strip. This strip was mounted in a constant temperature (37° C.) muscle bath having a volume of approximately 15 ml. The bathing medium was Krebs-Henseleit solution. Movement of the tracheal strip was measured by means of an isometric transducer connected to an electric recorder. The bath was aerated with a mixture of 95% carbon dioxide and 5% oxygen. Contractions were induced in the strips by the addition of a suitable amount of histamine, leukotriene C$_4$, acetylcholine or barium chloride. The amount of a given compound of Formula I (measured in mcg/ml) required to provide greater than 75% relaxation of drug-induced contraction is considered an effective concentration. For comparison, a well known standard bronchodilator, aminophylline (the ethylenediamine salt of theophylline), requires concentrations of 50 mcg/ml versus histamine, 100 mcg/ml versus acetylcholine and 10 mcg/ml versus barium chloride to provide greater than 75% relaxation.

The compounds of formula I which were most active in the above described in vitro test, including most of those listed above as preferred compounds, were tested in vivo in the guinea pig for bronchodilator activity using the so-called Konzett-Rossler in vivo test method. The activity was determined according to the procedure which follows. The Konzett-Rossler technique [H. Konzett and R. Rossler, Naunyn-Schmiedebergs Arch. Pharmakol., 195, 71-74 (1940)]was used to assess the effect of test drugs on antigen challenge of male Hartley strain guinea pigs (350-500 g). Sensitized (50 mg/kg ovalbumin, i.p., 14-21 days previously) or naive animals were anesthetized with pentobarbital (70 mg/kg, i.p.) and spontaneous respiration eliminated with succinylcholine (2 mg/kg i.p.). The trachea was cannulated and respiration maintained under positive pressure with a miniature ventilator (5 ml/breath, 87/minute, 10 cm water). Bronchoconstrictor responses were represented as increased excursions of the tracing on a physiological recorder of air overflow to the lungs measured by a pneumotachograph in series with a differential pressure transducer. Sensitized animals were challenged with ovalbumin (100 mcg/kg, i.v.) after the i.p. or p.o. administration of test drugs. Active compounds are those which demonstrate an intraperitoneal or oral $IC_{50}$ of 25 mg per kg or less, and preferably an $IC_{50}$ of 10 mg per kg or less. Most preferred compounds are active at 10 mg per kg.

The compounds of Formula I may be administered to mammals in order to obtain bronchodilation. The compounds may be administered orally, parenterally or by inhalation. Preferably they are administered orally in tablets or capsules. The usual effective human dose will be in the range of 0.1 to 50 mg/kg of body weight.

Salts of compounds of Formula I wherein A is methylene and B is methylene or —$CHR_9$— are generally prepared by reaction with an equimolar amount of a relatively strong acid, preferably an inorganic acid such as hydrochloric, sulfuric or phosphoric acid, in a polar solvent. Isolation of the salt is facilitated by the addition of a solvent in which the salt is insoluble, an example of such a solvent being diethyl ether.

The compounds of Formula I, either as the free base or in the form of a pharmaceutically acceptable acid addition salt, can be combined with conventional pharmaceutical diluents and carriers to form such dosage forms as tablets, capsules, suspensions, solutions, suppositories and the like.

The pharmaceutical carrier employed may be, for example, either a solid or liquid. Examples of solid carriers are lactose, terra alba, sucrose, talc, gelatin, agar, pectin, acacia, magnesium stearate, stearic acid, and the like. Liquid carriers include syrup, peanut oil, olive oil, water and the like. Similarly, the carrier or diluent can include a time delay material well known to the art, such as glyceryl monostearate or glyceryl distearate, these being employed alone or, for example, in combination with a wax.

When Y is N—$R_{10}$ or O, the compounds of Formula VI, which are subsets of compounds of Formula I, may be prepared according to Reaction Scheme I below, wherein the various substituents are as defined in the context of Formula I above with the exception that $R_7$ may only be hydrogen, alkyl or benzyl.

Reaction Scheme I

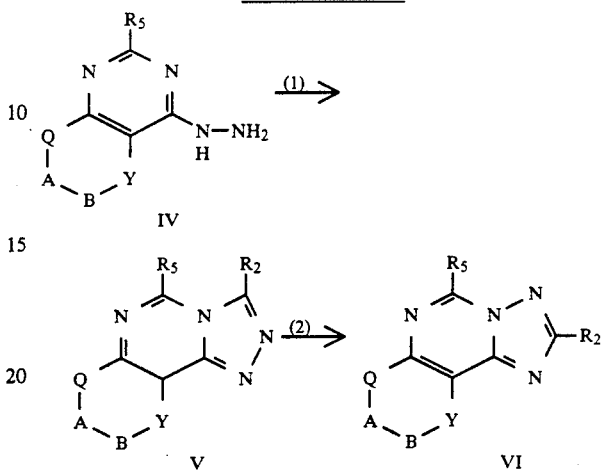

In step (1), a 4-hydrazinopyrimido[5,4-b][1,4]oxazine, or -[4,5-b][1,4]oxazine or -oxazinone of Formula IV, which can be prepared as described in Reaction Scheme II below, is reacted with an orthoester of the formula $R_2C(OAlk)_3$ to provide a novel compound of Formula V. Orthoesters of the formula $R_2C(OAlk)_3$ are well known and readily available. Examples of suitable orthoesters include trimethyl orthoformate, triethyl orthoformate, triethyl orthoacetate, triethyl orthopropionate and the like. Since the orthoesters are liquids, it is convenient to mix the compound of Formula IV with an excess of orthoester and to heat the mixture at reflux until reaction is complete.

In step (2), the compound of Formula V is heated with a suitable reagent to provide a product of Formula VI, a subset of the compounds of Formula I. This reaction is preferably carried out by heating the reaction mixture at its reflux temperature in a solvent inert to these conditions such as a lower alkanol. In general, the preferred reagents to effect the reaction of step (2) are alkali metal alkoxides such as sodium methoxide or sodium ethoxide, in catalytic amounts. It is also possible to use aqueous lower alkanoic acids such as formic acid, acetic acid and propionic acid to effect the reaction of step (2). The products of Formula VI, a subset of the compounds of Formula I, are isolated by conventional methods such as filtration, extraction or chromatography.

Compounds of either Formula V or VI, wherein $R_7$ is hydrogen, may be readily acetylated by conventional methods.

Compounds of Formula IV, appearing in Reaction Scheme I above, may be prepared according to Reaction Scheme II below wherein the various substituents are as defined in the context of Formula I above when Y is O or N—$R_{10}$ with the exception that $R_7$ may only be hydrogen, alkyl or benzyl. In this scheme, $Q_1$ and $Q_2$ are either N-H and O or O and N-H, respectively. In structures of the scheme of Formula VII or VIII either A or B, but not both simultaneously, must be carbonyl, while in structures IX and X, A and B can only be methylene or —$CHR_9$—.

Reaction Scheme II

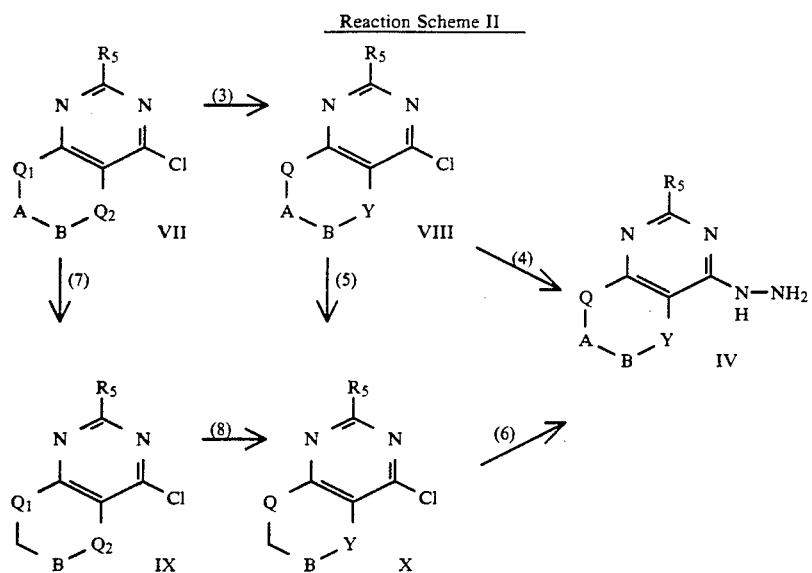

The compounds of Formula VII wherein Q₁ is NH, Q₂ is O, A is carbonyl and B is methylene or —CHR₉— are known and can be synthesized using the general procedure described by Sazonov, et al., Khimiya Geterotsiklicheskikh Soedinenii, 1973, 171; ibid., 1972, 1285, and ibid., 1976, 681, each of these three publications being incorporated herein by reference. Variations of the procedure described in these publications are conventional and involve primarily variations either in the starting amidine or in the added 2-haloalkanoic ester or acid.

The compounds of Formula VII wherein Q₁ is O, Q₂ is NH, A is methylene, and B is carbonyl, are also known, and can be synthesized using the general procedures described by Melik-Ogandzhanyan, et al., Khimiya Geterotsiklicheskikh Soedinenii, 1985, 974, incorporated herein by reference. Variations of the procedures described in this publication are conventional and involve primarily variations in the starting amidine.

In step (3) of Reaction Scheme II, a compound of Formula VII is reacted with a benzyl halide or an alkyl halide such as an alkyl iodide or alkyl bromide to provide a compound of Formula VIII. The reaction is conducted in a lower alkanol solvent in the presence of an alkali metal alkoxide such as sodium methoxide or in the solvent N,N-dimethylformamide in the presence of sodium hydride. The reaction mixture is generally heated at or near its reflux temperature in an alkanol solvent or from 20° to 50° C. in N,N-dimethylformamide.

When Q₁ is O and Q₂ is N-H the reaction preferably uses sodium hydride in N,N-dimethylformamide rather than an alkali metal alkoxide in an alkanol.

Step (4) involves the reaction of a compound of Formula VIII with hydrazine hydrate optionally in a lower alkanol solvent such as n-butyl alcohol to provide a novel intermediate of Formula IV.

The compounds of Formula IV wherein A is methylene and B is methylene or —CHR₉— can be made by sequential application of steps (5) and (6). In step (5), the amide compounds of Formula VIII are reduced to the amines of Formula X by reaction with a borane reagent. Generally, 4 moles of borane per mole of the compound of Formula VIII are employed, and the reaction is accompanied by heating at a temperature up to the reflux temperature of the mixture. The reaction is carried out in an inert solvent such as tetrahydrofuran and the borane reagent employed may be, for example, a methyl sulfide complex of borane in tetrahydrofuran.

In step (6), the amines of Formula X are reacted with hydrazine hydrate in the same fashion as in step (4) to provide the compounds of Formula IV.

The compounds of Formula X can also be provided by sequential application of steps (7) and (8). Thus in step (7), the amide VII is first reduced with a borane reagent, in a fashion similar to that of step (5), to obtain the compound of Formula IX. Alkylation of compound IX in step (8) then provides a compound of Formula X.

Compounds of Formula IV wherein R₇ is hydrogen are obtained by omitting the alkylation steps (3) or (8), and instead reacting either a compound of Formula VII or a compound of Formula IX with hydrazine hydrate, using the method of step (4).

When Y is S and A is carbonyl and B is methylene or —CHR₉—, the compounds of Formula XIX, which are a subset of compounds of Formula I, can be prepared according to Reaction Scheme III below, wherein the various substituents are as defined in the context of Formula I above with the exception that R₇ may only be alkyl or benzyl.

Reaction Scheme III

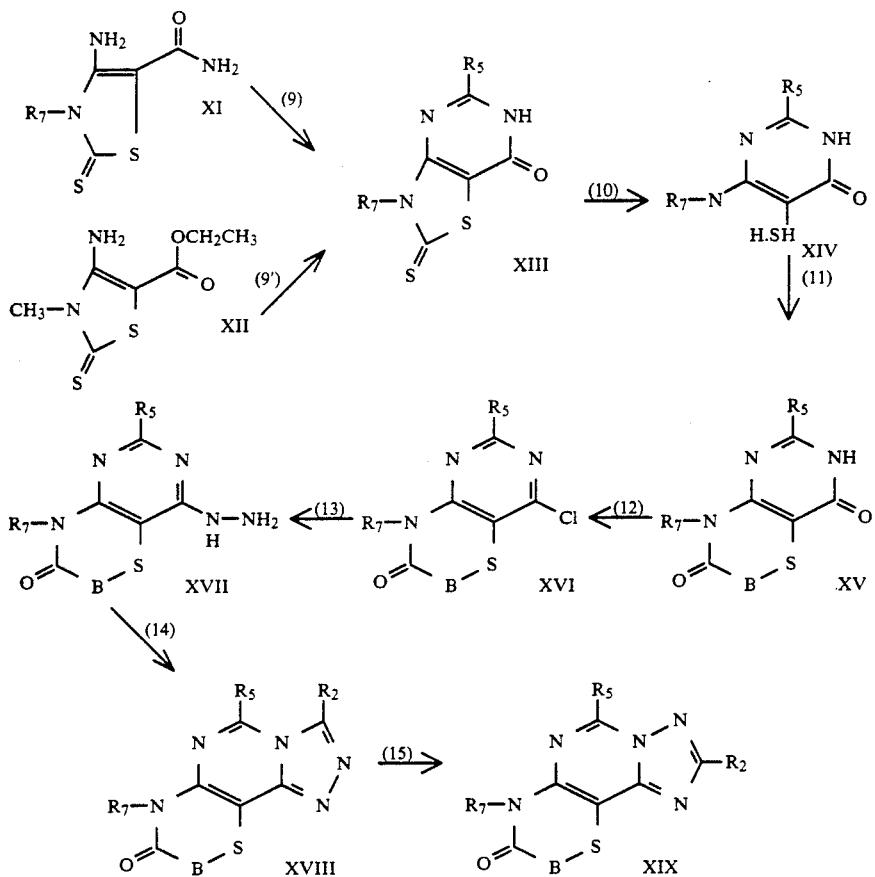

Compounds of structure XI, where R7 is lower alkyl or benzyl, are known and can be prepared as described by Gewald in J. Prakt. Chem., 32, 26–30 (1966), the disclosure of which is incorporated herein by reference. Compounds of Formula XIII are prepared in step (9) using Gewald's general procedure, but using an orthoester of the formula R5C(OAlk)3 rather than triethyl orthoformate.

An alternate route to the preparation of the compounds of Formula XIII can be employed and is shown in step (9'). It involves the synthetic process described by Gewald with the exception that the compound of Formula XII is reacted with acetamidine hydrochloride in a refluxing solvent, preferably a lower chain alcohol, containing 1.5 to 2.0 equivalents of sodium methoxide, to form the compounds of Formula XIII.

The reaction of step (10) to form the compounds of Formula XIV can be carried out according to the procedure of Gewald, J. Prakt. Chem., 32, 26–30 (1966), although only 5-mercapto-6-phenylamino-3H-pyrimidin-4-one was specifically described by him.

Step (11) to form the novel compounds of Formula XV is carried out by reacting a compound of Formula XIV with a 2-haloalkanoic acid in refluxing sodium hydroxide solution, followed by refluxing the resultant isolated intermediate in acetic anhydride to provide the compounds of Formula XV.

Step (12) involves reaction of the compounds of Formula XV with phosphorus oxychloride to provide the 4-chloro compounds of Formula XVI.

Step (13) involves reaction of hydrazine or hydrazine hydrate with the compounds of Formula XVI to provide the novel compounds of Formula XVII.

Step (14) involves reaction of a hydrazino compound of Formula XVII with an orthoester of the formula R2C(OAlk)3 to provide a novel compound of Formula XVIII. Orthoesters of the formula R2C(OAlk)3 are well known and readily available compounds or may be prepared by known methods. Specific examples of suitable orthoesters include trimethyl orthoformate, triethyl orthoformate, triethyl orthoacetate, triethyl orthopropionate and the like. Since the orthoesters are liquids, it is convenient to mix an excess of orthoester with the compound of Formula XVII and reflux until the desired compound of Formula XVIII is formed.

In step (15) the compound of Formula XVIII is rearranged by refluxing in a solution of a catalytic amount of methanolic sodium methoxide to form the compounds of Formula XIX, a subset of the compounds of Formula I, wherein A is carbonyl.

Compounds of Formula XIX are solids which may be readily isolated by conventional methods such as filtration, extraction or chromatography. Structural assignments may be confirmed by infrared and nuclear magnetic resonance spectral analyses.

When Y is S, A is methylene and B is methylene or —CHR9—, the compounds of Formula XXVI, which are a subset of compounds of Formula I, can be prepared according to Reaction Scheme IV below, wherein the various substituents are as defined in the context of Formula I above.

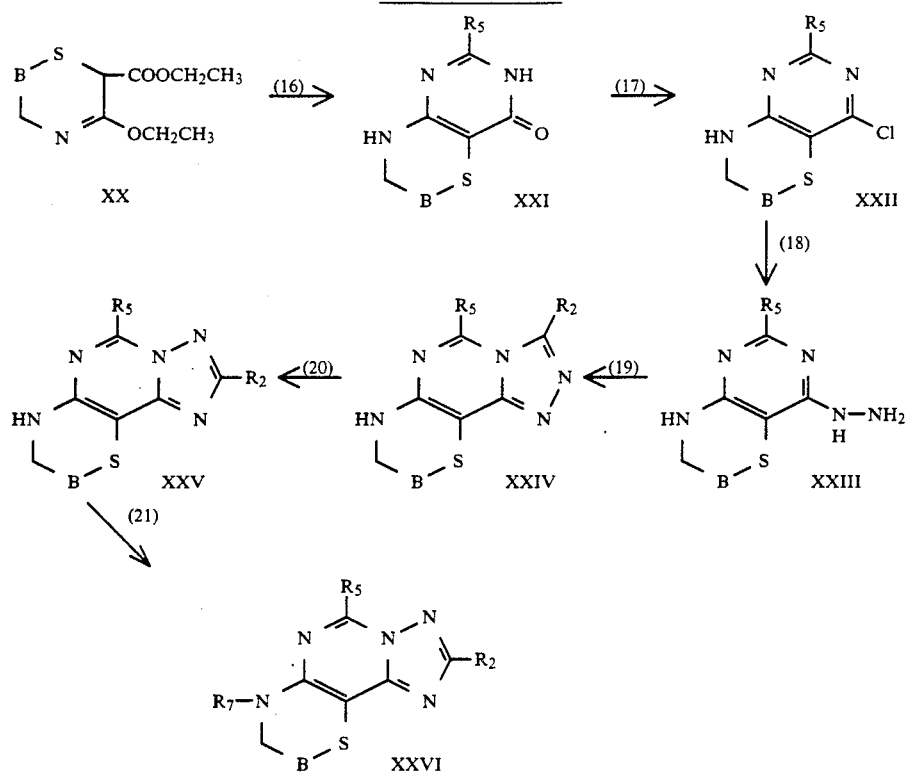

Reaction Scheme IV

The 5,6-dihydro-3-ethoxy-2-ethoxycarbonyl-2H[1,4]thiazines of Formula XX can be prepared according to the procedure of Great Britain patent application 2,143,234A and Henrie II, Robert N., Lazarus, Robert A., and Benkovic, Stephen J., J. Med. Chem., 26, No. 4, 559-563 (1983), the disclosures of both of which are incorporated herein by reference. The compound of Formula XX is reacted in step (16) with an amidine salt in a refluxing alcohol to which has been added 2.0 to 2.5 equivalents of sodium methoxide; thus forming the oxopyrimido[5,4-b][1,4]thiazines of Formula XXI.

Step (17) involves reaction of the compounds of Formula XXI with phosphorus oxychloride to provide the 4-chloro compounds of Formula XXII.

Step (18) involves reaction of hydrazine or hydrazine hydrate with the compounds of Formula XXII to provide the novel hydrazino compounds of Formula XXIII.

Step (19) involves reaction of a hydrazino compound of Formula XXIII with an orthoester of the formula $R_2C(OAlk)_3$ to provide a novel compound of Formula XXIV. Orthoesters of the formula $R_2C(OAlk)_3$ are well known and readily available compounds or may be prepared by known methods. Specific examples of suitable orthoesters include trimethyl orthoformate, triethyl orthoformate, triethyl orthoacetate, triethyl orthopropionate and the like. Since the orthoesters are liquids, it is convenient to mix an excess of orthoester with the compound of Formula XXIII and reflux until the desired compound of Formula XXIV is formed.

In step (20) the compound of Formula XXIV is rearranged by refluxing in a solution of a catalytic amount of methanolic sodium methoxide to form the compounds of Formula XXV.

Step (21) involves the further reaction of the 8,9-dihydro-1,2,4-triazolo[1,5-c]pyrimido[5,4-b][1,4]thiazines of Formula XXV with an alkyl, acyl or benzyl halide to form the compounds of Formula XXVI, which are a subset of compounds of Formula I. Although in the specific examples described herein alkylation was carried out using a compound of Formula XXV, alkylation could have also been carried out using a compound of either Formula XXII or Formula XXIV.

Compounds of Formula XXII, Formula XXIV, Formula XXV or Formula XXVI can be oxidized to their respective sulfoxides by reaction with sodium metaperiodate, or a peracid such as meta-chloroperbenzoic acid. Similarly, any of the compounds previously mentioned which are capable of oxidation to the sulfoxide may be independently oxidized to the sulfone by the action of a peracid such as metachloroperbenzoic acid. Alternatively, and sulfoxide may be further oxidized to form the corresponding sulfone.

All compounds of Formula XXVI, a subset of compounds of Formula I, are solids which may be readily isolated by conventional methods such as filtration, extraction or chromatography. Structural assignments may be confirmed by infrared and nuclear magnetic resonance spectral analyses.

The following examples are provided to illustrate the methods used in the invention. They are not intended to limit the invention.

EXAMPLE 1 with the indicated trialkyl orthoesters to provide novel intermediates of Formula V (TABLE IA).

TABLE IA

| Example | Orthoester | Intermediate of Formula V | | | | |
|---|---|---|---|---|---|---|
| | | $R_2$ | $R_5$ | $R_7$ | B | A |
| 2 | triethyl orthopropionate | $CH_2CH_3$ | $CH_3$ | H | $CH_2$ | C=O |
| 3 | triethyl orthoformate | H | $CH_2CH_3$ | $CH_2CH_3$ | $CH_2$ | C=O |
| 4 | triethyl orthopropionate | $CH_2CH_3$ | $CH_2CH_3$ | $CH_2CH_3$ | $CH_2$ | C=O |
| 5 | triethyl orthoformate | H | $CH_3$ | $CH_3$ | $CH_2$ | C=O |
| 6 | triethyl orthoacetate | $CH_3$ | $CH_2CH_3$ | $CH_2CH_3$ | $CH_2$ | C=O |
| 7 | triethyl orthoacetate | $CH_3$ | $CH_3$ | $CH_3$ | $CH_2$ | C=O |
| 8 | triethyl orthoacetate | $CH_3$ | $CH_2CH_3$ | $CH_3$ | $CH_2$ | C=O |
| 9 | triethyl orthoformate | H | $CH_2CH_3$ | $CH_3$ | $CH_2$ | C=O |
| 10 | triethyl orthopropionate | $CH_2CH_3$ | $CH_2CH_3$ | H | $CH_2$ | C=O |
| 11 | triethyl orthopropionate | $CH_2CH_3$ | $CH_3$ | H | $CHCH_2CH_3$ | C=O |
| 12 | triethyl orthopropionate | $CH_2CH_3$ | $CH_3$ | H | $CHCH_3$ | C=O |
| 13 | triethyl orthoacetate | $CH_3$ | $CH_3$ | H | $CHCH_3$ | C=O |
| 14 | triethyl orthopropionate | $CH_2CH_3$ | $CH_2CH_3$ | H | $CHCH_2CH_3$ | C=O |
| 15 | triethyl orthoacetate | $CH_3$ | $CH_2CH_3$ | H | $CHCH_2CH_3$ | C=O |
| 16 | triethyl orthopropionate | $CH_2CH_3$ | $CH_2CH_3$ | H | $CHCH_3$ | C=O |
| 17 | triethyl orthopropionate | $CH_2CH_3$ | $CH_2CH_3$ | $CH_3$ | $CH_2$ | C=O |
| 18 | triethyl orthopropionate | $CH_2CH_3$ | $CH_3$ | H | $CH_2$ | $CH_2$ |
| 19 | triethyl orthoformate | H | $CH_3$ | $CH_2CH_3$ | $CH_2$ | $CH_2$ |
| 20 | triethyl orthoacetate | $CH_3$ | $CH_3$ | $CH_2CH_3$ | $CH_2$ | $CH_2$ |
| 21 | triethyl orthopropionate | $CH_2CH_3$ | $CH_3$ | $CH_2CH_3$ | $CH_2$ | $CH_2$ |
| 22 | triethyl orthopropionate | $CH_2CH_3$ | $CH_3$ | $CH_3$ | $CH_2$ | $CH_2$ |

Step 1

Preparation of 8,9-Dihydro-5,7-dimethyl-3-ethyl-1,2,4-triazolo[4,3-c]pyrimido[5,4-b][1,4]oxazin-8-one A mixture of 4.0g (0.019 mole) of 6,7-dihydro-2,8-dimethyl-4-hydrazinopyrimido[5,4-b][1,4]oxazin-7-one and 25 ml of triethyl propionate was heated first at 110° C. for about 16 hours and then at 130° C. for an additional 25.5 hours. The mixture was evaporated by passing a stream of nitrogen gas over it, and 1.0g of the solid residue was separated for reaction in Step 2. The remainder of the residue was dissolved in dichloromethane and passed through a silica flash chromatography column, eluting sequentially with ethyl acetate and acetone. The fractions were checked by thin layer chromatography, and were evaporated to provide solid fractions. A later fraction which showed only one component was determined to be 8,9-dihydro-5,7-dimethyl-3-ethyl-1,2,4-triazolo[4,3-c]pyrimido[5,4-b][1,4]-oxazin-8-one, m.p. 200° C. Analysis: Calculated for $C_{11}H_{13}N_5O_2$: %C, 53.4; %H, 5.3; %N, 28.3: Found: %C, 53.4; %H, 5.3; %N, 28.4.

EXAMPLES 2–22

Using the method of Step 1, Example 1, the indicated intermediates of Formula IV wherein Y is O, Q is N—$R_7$ and B is methylene or —$CHR_9$— were reacted

EXAMPLES 23–40

Using the method of step 1, Example 1, the indicated intermediates of Formula IV wherein Y is N—$R_{10}$, Q is O, and A is methylene were reacted with the indicated trialkyl orthoesters to provide novel intermediates of Formula V (Table IB). Example 39 has not actually been carried out.

TABLE IB

| Example | Orthoester | Intermediate of Formula V | | | |
|---|---|---|---|---|---|
| | | $R_2$ | $R_5$ | $R_{10}$ | B |
| 23 | triethyl orthoacetate | $CH_3$ | $CH_3$ | $CH_3$ | C=O |
| 24 | triethyl orthopropionate | $CH_2CH_3$ | $CH_3$ | $CH_3$ | $CH_2$ |
| 25 | triethyl orthoacetate | $CH_3$ | $CH_3$ | $CH_3$ | $CH_2$ |
| 26 | triethyl orthopropionate | $CH_2CH_3$ | $CH_3$ | $CH_3$ | C=O |
| 27 | triethyl orthoacetate | $CH_3$ | $CH_2CH_3$ | $CH_3$ | $CH_2$ |
| 28 | triethyl orthopropionate | $CH_2CH_3$ | $CH_2CH_3$ | $CH_3$ | $CH_2$ |
| 29 | triethyl orthopropionate | $CH_2CH_3$ | $CH_2CH_3$ | $CH_3$ | C=O |
| 30 | triethyl orthoacetate | $CH_3$ | $CH_2CH_3$ | $CH_2CH_3$ | $CH_2$ |
| 31 | triethyl orthopropionate | $CH_2CH_3$ | $CH_2CH_3$ | $CH_2CH_3$ | $CH_2$ |

TABLE IB-continued

| Example | Orthoester | Intermediate of Formula V | | | |
|---|---|---|---|---|---|
| | | $R_2$ | $R_5$ | $R_{10}$ | B |
| 32 | triethyl orthoacetate | $CH_3$ | $CH_2CH_3$ | $CH_3$ | C=O |
| 33 | triethyl orthoacetate | $CH_3$ | $CH_2CH_3$ | $CH_2CH_3$ | C=O |
| 34 | triethyl orthoacetate | $CH_3$ | $CH_3$ | $CH_2Ph$ | $CH_2$ |
| 35 | triethyl orthopropionate | $CH_2CH_3$ | $CH_3$ | $CH_2Ph$ | $CH_2$ |
| 36 | triethyl orthoacetate | $CH_3$ | $CH_3$ | $CH_2CH_3$ | $CH_2$ |
| 37 | triethyl orthopropionate | $CH_2CH_3$ | $CH_3$ | $CH_2CH_3$ | $CH_2$ |
| 38 | triethyl orthopropionate | $CH_2CH_3$ | $CH_2CH_3$ | $CH_2CH_3$ | C=O |
| 39 | triethyl orthoformate | H | $CH_3$ | $CH_3$ | C=O |
| 40 | triethyl orthoformate | H | $CH_3$ | $CH_2CH_3$ | $CH_2$ |

EXAMPLE 41

Step 2

Preparation of
8,9-Dihydro-5,7-dimethyl-2-ethyl-1,2,4-triazolo[1,5-c]pyrimido[5,4-b][1,4]oxazin-8-one One gram (4.05 mmole) of crude 8,9-dihydro-5,7-dimethyl-3-ethyl-1,2,4-triazolo[4,3-c]pyrimido[5,4-b][1,4]-oxazin-8-one obtained in Step 1, Example 1 was dissolved in 20 ml of methanol. Two drops of 25% sodium methoxide solution were added and the solution was heated at its reflux temperature for one hour. The solution was evaporated under vacuum and the residue was dissolved in dichloromethane and eluted through a flash chromatography column with 1:1 (by volume) dichloromethane:ethyl acetate to obtain a white solid which was recrystallized from a benzene-hexane mixture to provide 8,9-dihydro-5,7-dimethyl-2-ethyl-1,2,4-triazolo[1,5-c]pyrimido[5,4-b][1,4]oxazin-8-one, m.p. 169-170° C. Analysis: Calculated for $C_{11}H_{13}N_5O_2$: %C, 53.4; %H, 5.3; %N, 28.3; Found: %C, 53.4; %H, 5.2; %N, 28.5.

EXAMPLES 42-62

Using the method of Step 2, Example 41, the indicated intermediate of Formula V wherein Y is O, Q is N—$R_7$ and B is methylene or —$CHR_9$— was reacted with methanolic sodium methoxide to provide the indicated product of Formula VI (TABLE IIA).

TABLE IIA

| Example | Intermediate from Example | Product of Formula VI | | | | | Calculated: %C; %H; %N Found: %C; %H; %N (m.p. in °C.) | |
|---|---|---|---|---|---|---|---|---|
| | | $R_2$ | $R_5$ | $R_7$ | B | A | | |
| 42 | 2 | $CH_2CH_3$ | $CH_3$ | H | $CH_2$ | C=O | 51.5; 4.75; 51.5; 4.7; (284-285) | 30.0 30.0 |
| 43 | 3 | H | $CH_2CH_3$ | $CH_2CH_3$ | $CH_2$ | C=O | 53.4; 5.3; 53.8; 5.5; (113-114) | 28.3 28.3 |
| 44 | 4 | $CH_2CH_3$ | $CH_2CH_3$ | $CH_2CH_3$ | $CH_2$ | C=O | 54.9; 6.4; [· ½ $H_2O$]; 55.4; 6.1; (78-80) | 24.6 24.5 |
| 45 | 5 | H | $CH_3$ | $CH_3$ | $CH_2$ | C=O | 49.3; 4.1; 49.3; 4.2; (210-211) | 31.95 31.8 |
| 46 | 6 | $CH_3$ | $CH_2CH_3$ | $CH_2CH_3$ | $CH_2$ | C=O | 55.2; 5.8; 55.3; 5.8; (153-154) | 26.8 26.9 |
| 47 | 7 | $CH_3$ | $CH_3$ | $CH_3$ | $CH_2$ | C=O | 51.5; 4.75; 51.5; 4.7; | 30.0 30.1 |
| 48 | 8 | $CH_3$ | $CH_2CH_3$ | $CH_3$ | $CH_2$ | C=O | 53.4; 5.3; 53.3; 5.3; (201-202) | 28.3 28.4 |
| 49 | 9 | H | $CH_2CH_3$ | $CH_3$ | $CH_2$ | C=O | 51.5; 4.75; 51.7; 4.8; (174-175) | 30.0 29.9 |
| 50 | 10 | $CH_2CH_3$ | $CH_2CH_3$ | H | $CH_2$ | C=O | 53.4; 5.3; 53.2; 5.4; (231-233) | 28.3 28.0 |
| 51 | 11 | $CH_2CH_3$ | $CH_3$ | H | $CHCH_2CH_3$ | C=O | 55.2; 5.8; 54.9; 5.6; (185-186) | 26.8 26.7 |
| 52 | 12 | $CH_2CH_3$ | $CH_3$ | H | $CHCH_3$ | C=O | 53.4; 5.3; 53.4; 5.4; (145-146) | 28.3 28.7 |
| 53 | 13 | $CH_3$ | $CH_3$ | H | $CHCH_3$ | C=O | 51.5; 4.75; 51.0; 4.8; (149-151) | 30.0 30.2 |
| 54 | 14 | $CH_2CH_3$ | $CH_2CH_3$ | H | $CHCH_2CH_3$ | C=O | 56.7; 6.2; 56.4; 6.3; (217-218) | 25.4 25.7 |
| 55 | 15 | $CH_3$ | $CH_2CH_3$ | H | $CHCH_2CH_3$ | C=O | 55.2; 5.8; 54.7; 5.8; (208-209) | 26.8 26.4 |
| 56 | 16 | $CH_2CH_3$ | $CH_2CH_3$ | H | $CHCH_3$ | C=O | 55.2; 5.8; 54.6; 5.8; | 26.8 26.8 |

TABLE IIA-continued

| Example | Intermediate from Example | Product of Formula VI R$_2$ | R$_5$ | R$_7$ | B | A | Calculated: % C; % H; % N<br>Found: % C; % H; % N<br>(m.p. in °C.) | | |
|---|---|---|---|---|---|---|---|---|---|
| 57 | 17 | CH$_2$CH$_3$ | CH$_2$CH$_3$ | CH$_3$ | CH$_2$ | C=O | (229-230)<br>55.2; 5.8;<br>55.3; 5.8; | | 26.8<br>26.9 |
| 58 | 18 | CH$_2$CH$_3$ | CH$_3$ | H | CH$_2$ | CH$_2$ | (138-139)<br>54.8; 6.0;<br>54.9; 6.0; | | 31.9<br>31.7 |
| 59 | 19 | H | CH$_3$ | CH$_2$CH$_3$ | CH$_2$ | CH$_2$ | (173-175)<br>54.8; 6.0;<br>54.8; 6.1; | | 31.9<br>31.9 |
| 60 | 20 | CH$_3$ | CH$_3$ | CH$_2$CH$_3$ | CH$_2$ | CH$_2$ | (133-134)<br>56.6; 6.5;<br>57.0; 6.6; | | 30.0<br>30.3 |
| 61 | 21 | CH$_2$CH$_3$ | CH$_3$ | CH$_2$CH$_3$ | CH$_2$ | CH$_2$ | (137-138)<br>58.3; 6.9;<br>58.3; 6.9; | | 28.3<br>28.6 |
| 62 | 22 | CH$_2$CH$_3$ | CH$_3$ | CH$_3$ | CH$_2$ | CH$_2$ | (119-120)<br>56.6; 6.5;<br>56.4; 6.5;<br>(135-136) | | 30.0<br>30.0 |

EXAMPLES 63-78

Using the method of Step 2, Example 41, the indicated intermediate of Formula V wherein Y is N-R$_{10}$, Q is O and A is methylene was reacted with methanolic sodium methoxide to provide the indicated product of Formula VI (TABLE IIB).

TABLE IIB

| Example | Intermediate from Example | Product of Formula VI R$_2$ | R$_5$ | R$_{10}$ | B | Calculated: % C; % H; % N<br>Found: % C; % H; % N<br>(m.p. in °C.) | |
|---|---|---|---|---|---|---|---|
| 63 | 23 | CH$_3$ | CH$_3$ | CH$_3$ | C=O | 51.5; 4.75;<br>51.7; 4.8;<br>(193-194) | 30.0<br>29.8 |
| 64 | 24 | CH$_2$CH$_3$ | CH$_3$ | CH$_2$ | CH$_2$ | 56.6; 6.5;<br>56.7; 6.5;<br>(97-98) | 30.0<br>30.2 |
| 65 | 25 | CH$_3$ | CH$_3$ | CH$_3$ | CH$_2$ | 54.8; 6.0;<br>54.5; 6.0;<br>(140-141) | 31.9<br>31.8 |
| 66 | 27 | CH$_3$ | CH$_2$CH$_3$ | CH$_3$ | CH$_2$ | 56.6; 6.5;<br>56.5; 6.4;<br>(123-124.5) | 30.0<br>30.0 |
| 67 | 28 | CH$_2$CH$_3$ | CH$_2$CH$_3$ | CH$_3$ | CH$_2$ | 58.3; 6.9;<br>58.0; 6.9;<br>(67-70) | 28.3<br>28.5 |
| 68 | 29 | CH$_2$CH$_3$ | CH$_2$CH$_3$ | CH$_3$ | C=O | 55.2; 5.8;<br>55.3; 5.8;<br>(81-82) | 26.8<br>27.0 |
| 69 | 30 | CH$_3$ | CH$_2$CH$_3$ | CH$_2$CH$_3$ | CH$_2$ | 58.3; 6.9;<br>58.6; 7.0;<br>(81-82) | 28.3<br>28.6 |
| 70 | 31 | CH$_2$CH$_3$ | CH$_2$CH$_3$ | CH$_2$CH$_3$ | CH$_2$ | 59.7; 7.3;<br>59.2; 7.3;<br>(60-62.5) | 26.8<br>26.7 |
| 71 | 32 | CH$_3$ | CH$_2$CH$_3$ | CH$_3$ | C=O | 53.4; 5.3;<br>53.5; 5.3;<br>(133-134) | 28.3<br>28.2 |
| 72 | 35 | CH$_2$CH$_3$ | CH$_3$ | CH$_2$Ph | CH$_2$ | 66.0; 6.2;<br>65.8; 6.2;<br>(89-90) | 22.6<br>22.1 |
| 73 | 36 | CH$_3$ | CH$_3$ | CH$_2$CH$_3$ | CH$_2$ | 56.6; 6.5;<br>56.6; 6.6;<br>(111-113) | 30.0<br>30.3 |
| 74 | 34 | CH$_3$ | CH$_3$ | CH$_2$Ph | CH$_2$ | 65.1; 5.8;<br>64.7; 5.8;<br>(92-95) | 23.7<br>23.6 |
| 75 | 37 | CH$_2$CH$_3$ | CH$_3$ | CH$_2$CH$_3$ | CH$_2$ | 58.3; 6.9;<br>58.5; 7.0;<br>(83-84) | 28.3<br>28.6 |
| 76 | 33 | CH$_3$ | CH$_2$CH$_3$ | CH$_2$CH$_3$ | C=O | 55.2; 5.8;<br>55.2; 5.8;<br>(120-121) | 26.8<br>26.9 |
| 77 | 38 | CH$_2$CH$_3$ | CH$_2$CH$_3$ | CH$_2$CH$_3$ | C=O | 56.7; 6.2;<br>56.8; 6.2;<br>(73.5-76) | 25.4<br>25.5 |
| 78 | 40 | H | CH$_3$ | CH$_2$CH$_3$ | CH$_2$ | 54.8; 6.0;<br>55.0; 6.0; | 31.9<br>32.3 |

TABLE IIB-continued

| Example | Intermediate from Example | Product of Formula VI | | | | Calculated: % C; % H; % N<br>Found: % C; % H; % N<br>(m.p. in °C.) |
|---|---|---|---|---|---|---|
| | | $R_2$ | $R_5$ | $R_{10}$ | B | |
| | | | | | | (85–88) |

EXAMPLE 79

Preparation of 8,9-Dihydro-2,5-dimethyl-7-ethyl-1,2,4-triazolo[1,5 c]pyrimido[5,4-b][1,4]oxazine dihydrogen sulfate One gram (4.3 mmole) of 8,9-dihydro-2,5 dimethyl-7 ethyl-1,2,4-triazolo[1,5-c]pyrimido[5,4-b][1,4]oxazine, obtained in Example 42, was dissolved in 5 ml of ethanol. Concentrated sulfuric acid (0.42g, 4.3 mmole) was added, followed by the addition of diethyl ether to precipitate a white solid which was filtered, washed with diethyl ether and then dried to provide 8,9-dihydro-2,5-dimethyl-7-ethyl-1,2,4-triazolo[1,5-c]pyrimido[5,4-b][1,4]oxazine dihydrogen sulfate, m.p. 245°–246° C. Analysis: Calculated for $C_{11}H_{15}N_5O \cdot H_2SO_4$: %C, 39.9; %H, 5.2; %N, 21.1; Found: %C, 40.3; %H, 5.4; %N, 20.7.

EXAMPLE 80

Step 3

Preparation of 4-Chloro-6,7-dihydro-2,8-dimethylpyrimido[5,4-b][1,4]oxazin-7-one Using the method of Sazonov, et al., Khimiya Geterotsiklicheskikh Soedinenii, 9, 1285-1288 (1972), 4-chloro-6,7-dihydro-2-methyl-8H-pyrimido[5,4-b][1,4]oxazin-7-one was prepared. To a mixture of 8.0g (0.0402 mole) of 4-chloro-6,7-dihydro-2-methyl-8H-pyrimido[5,4-b][1,4]oxazin-7-one and 17.9 ml of methyl iodide was added 8.75g of 25% sodium methoxide in 250 ml of methanol, and the solution was heated at its reflux temperature for three hours. The solvent was removed by evaporation under vacuum, and the solid was separated by filtration, washed with water, and dried. The yellow solid was 4-chloro 6,7-dihydro-2,8-dimethylpyrimido[5,4-b][1,4]oxazin-7-one, m.p. 142°–143° C.

EXAMPLE 81

To a stirred suspension of 5g (0.023 mole) of 4-chloro-6,7-dihydro-2-ethyl-5H-pyrimido[4,5-b][1,4]oxazin-6-one (prepared using the method of Melik-Ogandzhanyan, et al., Khimiya Geterotsiklicheskikh Soedinenii, 1985, 974) in 100ml of N,N-dimethylformamide was added 0.75g (0.025 mole) of 80% sodium hydride in oil. After ten minutes 3.5g (0.025 mole) of methyl iodide was added. After two hours the solution was diluted with about 400ml of water, and extracted thrice with 250ml portions of chloroform. The extracts were washed with water, dried over magnesium sulfate, treated with decolorizing charcoal, and evaporated in vacuo. The resulting oil was triturated with a mixture of diethyl ether and hexanes to provide light green solid 4-chloro-6,7-dihydro-2-ethyl-5-methylpyrimido[4,5-b][1,4]oxazin-6-one.

EXAMPLES 82–84

Using the method described in Example 81 the following compounds of Formula VIII wherein Q is O, A is methylene and B is carbonyl were prepared.

| Example | Product of Formula VIII | |
|---|---|---|
| | $R_5$ | $R_{10}$ |
| 82 | $CH_3$ | $CH_2CH_3$ |
| 83 | $CH_2CH_3$ | $CH_2CH_3$ |
| 84 | $CH_3$ | $CH_3$ |

EXAMPLE 85

Using the procedure of Example 80, 4-chloro 6,7-dihydro-2-ethyl-8H-pyrimido[5,4-b][1,4]oxazin-7-one was alkylated providing 4-chloro-6,7-dihydro-2-ethyl-8-methylpyrimido[5,4-b][1,4]oxazin-7-one.

EXAMPLE 86

Using the procedure of Example 80, except that 1-bromoethane was used instead of methyl iodide, 4-chloro-6,7-dihydro 2-ethyl-8H-pyrimido[5,4-b][1,4]oxazin-7-one was alkylated providing 4-chloro-2,8-diethyl-6,7-dihydropyrimido[5,4-b][1,4]oxazin-7-one.

EXAMPLE 87

Step 4

Preparation of 6,7-Dihydro-2,8-dimethyl-4-hydrazinopyrimido[5,4-b][1,4]oxazin-7-one To a solution of 5.78g (0.0271 mole) of 4-chloro-6,7-dihydro-2,8-dimethylpyrimido[5,4-b][1,4]oxazin-7-one, obtained from Example 80, in 100 ml of n-butyl alcohol was added 1.74g (0.0543 mole) of hydrazine hydrate, and the mixture was heated at its reflux temperature for three hours. On cooling a solid precipitated and was separated by filtration, washed with water and dried. The structure of the light yellow product was 6,7-dihydro-2,8-dimethyl-4-hydrazinopyrimido[5,4-b][1,4]oxazin-7-one according to infrared spectral analysis.

EXAMPLES 88–89

Using the procedure of Example 87, the intermediates of Example 85 and Example 86 were independently reacted with hydrazine hydrate to provide the novel compounds 6,7-dihydro-2-ethyl-4-hydrazino-8-methyl-pyrimido[5,4-b][1,4]oxazin-7-one and 2,8-diethyl-6,7-dihydro-4-hydrazinopyrimido[5,4-b][1,4]oxazin-7-one respectively.

EXAMPLES 90–98

The method of Sazonov, et al., Khimiya Gotsiklicheskikh Soedinenii, 9, 1285≈1288 (1972), was used to prepare the 4-chloropyrimido[5,4 b][1,4]oxazin-7-ones which were independently reacted with hydrazine hydrate, according to the procedure of Example 87, to provide the novel compounds of Formula IV (TABLE IIIA).

TABLE IIIA

| | Compound of Formula IV | | |
|---|---|---|---|
| Example | $R_5$ | $R_7$ | B |
| 90 | $CH_3$ | $CH_3$ | $CH_2$ |
| 91 | $CH_3$ | H | $CH_2$ |
| 92 | $CH_2CH_3$ | $CH_2CH_3$ | $CH_2$ |
| 93 | $CH_2CH_3$ | $CH_3$ | $CH_2$ |
| 94 | $CH_2CH_3$ | H | $CH_2$ |
| 95 | $CH_3$ | H | $CHCH_2CH_3$ |
| 96 | $CH_3$ | H | $CHCH_3$ |
| 97 | $CH_2CH_3$ | H | $CHCH_2CH_3$ |
| 98 | $CH_2CH_3$ | H | $CHCH_3$ |

EXAMPLES 99–101

The method of step 4, Example 87 was used to prepare the novel compounds of Formula IV wherein Q is O, Y is N-$R_{10}$ and A is methylene as shown in Table IIIB.

TABLE IIIB

| | Intermediate | Compound of Formula IV | |
|---|---|---|---|
| Example | from Example | $R_5$ | $R_7$ |
| 99 | 84 | $CH_3$ | $CH_3$ |
| 100 | 83 | $CH_2CH_3$ | $CH_2CH_3$ |
| 101 | 81 | $CH_2CH_3$ | $CH_3$ |

EXAMPLE 102

Step 5

Preparation of 4-Chloro-6,7-dihydro-8-ethyl-2-methylpyrimido[5,4-b[]1,4]oxazine A solution of 2.0g (8.81 mmole) of 4 chloro-6,7-dihydro-8-ethyl-2-methylpyrimido[5,4-b][1,4]oxazin-7-one in 25 ml of tetrahydrofuran was added dropwise to 3.5 ml of cold (0° C.) borane-methyl sulfide complex in tetrahydrofuran. After the completion of the addition, the mixture was heated at its reflux temperature for three hours. The mixture was cooled and 14 ml of 6N hydrochloric acid was slowly added. This mixture was heated for one hour at 115° C., and was then cooled and neutralized with ammonium hydroxide. The mixture was extracted with chloroform, and the organic layer was then dried and evaporated to provide an oil residue which crystallized on cooling. Nuclear magnetic resonance spectral analysis showed the product to be 4-chloro-6,7-dihydro-8-ethyl-2-methylpyrimido[5,4-b][1,4]oxazine.

EXAMPLES 103–104

Using the method of Example 102, 4-chloro-6,7-dihydro-2,8-dimethylpyrimido[5,4-b][1,4]oxazin-7-one and 4-chloro-6,7-dihydro-2-methyl-8H-pyrimido[5,4b][1,-4]oxazin 7-one were reduced to white solids 4-chloro-6,7-dihydro-2,8 dimethylpyrimido[5,4-b][1,4]oxazine and 4-chloro 6,7-dihydro-2 methyl-8H-pyrimido[5,4-b][1,4]oxazine, respectively.

EXAMPLE 105

Step 6

Preparation of 6,7 Dihydro-8-ethyl-4-hydrazino-2-methylpyrimido[5,4-b][1,4]oxazine Using the method of Example 87, 4-chloro-6,7-dihydro-8-ethyl-2 methylpyrimido[5,4-b][1,4]oxazine, from Example 102, was reacted with hydrazine hydrate to provide 6,7-dihydro 8-ethyl-4-hydrazino 2-methylpyrimido[5,4-b][1,4]oxazine.

EXAMPLES 106–107

Using the procedure of Example 105, the indicated intermediates of Formula X were reacted with hydrazine hydrate to provide the compounds of Formula IV wherein Y is O, Q is N-$R_7$, and A and B are methylene (TABLE IV).

TABLE IV

| | Intermediate from | Intermediate of Formula X and Compound of Formula IV | |
|---|---|---|---|
| Example | Example | $R_5$ | $R_7$ |
| 106 | 103 | $CH_3$ | $CH_3$ |
| 107 | 104 | $CH_3$ | H |

EXAMPLE 108

Step 9

Preparation of 5-Ethyl-3-methyl-6H-thiazolo[4,5-d]pyrimidin-7-one-2-thione

The general procedure of Gewald, J. Prakt. Chem., 32, 26–30 (1966) was used to prepare 4-amino 3-methylthiazoline-2-thione-5-carboxamide, of which 27.3 g (0.14 mole) was suspended in a mixture of approximately 144ml of acetic anhydride and about 144ml of triethyl orthopropionate. The resultant mixture was refluxed for approximately one half hour, then cooled in an ice bath. The solid which precipitated was separated by filtration, washed with diethyl ether and dried in a vacuum oven at approximately 100° C. to provide 21.4g (65%) of 5-ethyl-3-methyl-6H-thiazolo[4,5-d]pyrimidin-7-one-2-thione. Infrared spectral analysis confirmed the structural assignment.

EXAMPLES 109 AND 110

Utilizing the procedure of Example 108, the designated intermediates of Formula XI were reacted with triethyl orthopropionate to provide the corresponding compounds of Formula XIII listed in TABLE V, the structures of which were confirmed by the indicated spectral analysis.

TABLE V

| Example | Intermediate of Formula XI and Compounds of Formula XIII $R_7$ | Reflux Time (in min.) | Yield (%) | Spectral Analysis |
|---|---|---|---|---|
| 109 | $(CH_2)_3CH_3$ | 30 | 59 | IR, NMR |
| 110 | $CH_2Ph$ | 30–60 | 53 | IR, NMR |

EXAMPLE 111

Step 9

Preparation of 3,5-Dimethyl-6H-thiazolo[4,5-d]pyrimidin-7-one-2-thione

Ethyl 4-amino-3-methylthiazoline-2-thione-5-carboxylate (1.4g, 6.4 mmoles), prepared according to the procedure of Gewald, J. Prakt. Chem., 32, 26–30 (1966), was suspended in approximately 40ml of ethanol. Acetamidine hydrochloride (0.6g, 6.4 mmole) and 2.77g (12.8 mmole) of a 25% solution of sodium methoxide in methanol were added to the suspension and the resultant mixture refluxed for approximately 20 hours. The ethanol was removed in vacuo and the residue was suspended in water and neutralized with concentrated hydrochloric acid. The resultant precipitate was filtered and dried to provide 1 g of 3,5-dimethyl-6H-thiazolo[4,5-d]pyrimidin-7-one-2-thione. The structural assignment was confirmed by nuclear magnetic resonance spectral analysis.

EXAMPLE 112

Step 10

Preparation of 2-Ethyl-5-mercapto-6-methylamino-3H-pyrimidin-4-one

5-Ethyl-3-methyl-6H-thiazolo[4,5-d]pyrimidin-7-one-2-thione (9.5g, 41.8 mmole) from Example 108 was suspended in approximately 500ml of 4N sodium hydroxide solution. The resultant mixture was refluxed for 2 to 4 hours, followed by cooling at approximately 4° C. for about 20 hours. The mixture was slowly acidified with concentrated hydrochloric acid; the solid was separated by filtration and dried, providing 6.6g (85%) of 2-ethyl-5-mercapto-6-methylamino-3H-pyrimidin-4-one. Infrared and nuclear magnetic resonance spectral analyses confirmed the structural assignment.

EXAMPLES 113 AND 114

Using the procedure of Example 112, the intermediates of Formula XIII were refluxed in sodium hydroxide solution, then acidified to provide the compounds of Formula XIV listed in TABLE VI, the structures of which were confirmed by the indicated spectral analysis.

TABLE VI

| Example | Intermediate from Example | Intermediate of Formula XIII and Compound of Formula XIV $R_7$ | Yield (%) | Spectral Analysis |
|---|---|---|---|---|
| 113 | 109 | $(CH_2)_3CH_3$ | 98 | IR, NMR |
| 114 | 110 | $CH_2Ph$ | 96 | IR, NMR |

EXAMPLE 115

Step 11

Preparation of 6,7-Dihydro-2-ethyl-8-methyl-3H-pyrimido[5,4-b][1,4]thiazine-4,7-dione 2-Ethyl-5-mercapto-6-methylamino-3H-pyrimidin4-one (6.6g, 0.036 mole) from Example 112 and 3.37g (0.036 mole) of chloroacetic acid were added to approximately 120ml of water containing 4.27g (0.107 mole) of sodium hydroxide. The resultant solution was refluxed for approximately 4 hours, allowed to cool and acidified to about pH 2 with concentrated hydrochloric acid. The white solid was separated by filtration and dried (7.4g), then refluxed in approximately 100ml of acetic anhydride for about 2 hours and allowed to cool. The precipitate was removed by suction filtration, washed with diethyl ether and dried, providing 6.26g (78%) of 6,7 dihydro-2-ethyl-8-methyl-3H-pyrimido[5,4-b][1,4]thiazine-4,7-dione. The structural assignment was confirmed by infrared spectral analysis.

EXAMPLES 116 AND 117

Utilizing the method of Example 115, the intermediates of Formula XIV were converted to the compounds of Formula XV listed in TABLE VII, the structures of which were confirmed by the indicated spectral analysis.

TABLE VII

| Example | Intermediate from Example | Intermediate of Formula XIV and Compound of Formula XV $R_7$ | Yield (%) | Spectral Analysis |
|---|---|---|---|---|
| 116 | 113 | $(CH_2)_3CH_3$ | 36 | IR, NMR |
| 117 | 114 | $CH_2Ph$ | 41 | IR, NMR |

EXAMPLE 118

2-Ethyl-5-mercapto-6-benzylamino-3H-pyrimidin-4-one (10.0g, 0.038 mole) from Example 114 was suspended in approximately 100ml of water containing 4.6g (0.115 mole) of sodium hydroxide and the suspension was stirred for about 10 minutes. 2-Bromobutyric acid (6.39g, 0.038 mole) was added and the resultant mixture refluxed for about 2 hours, allowed to cool and acidified to approximately pH 4–5 with concentrated hydrochloric acid. The precipitate was separated by filtration and dried providing 8.8g which was suspended in approximately 100ml of acetic anhydride, refluxed for about one hour and then allowed to cool. Since no solid precipitated on cooling, a stream of nitrogen was blown over the solution to evaporate the acetic anhydride. The residue was then dissolved in methylene chloride and flash chromatographed, eluting with 1:10 (by volume) ethyl acetate:methylene chloride. Evaporation provided 3.0g (24%) of yellow solid, 2,6-diethyl-6,7-dihydro-8-benzyl-3H-pyrimido[5,4-b][1,4]thiazine-4,7 dione. Infrared spectral-analysis confirmed the structural assignment.

EXAMPLE 119

Step 12

Preparation of 4-Chloro-6,7 dihydro-2-ethyl-8-methylpyrimido[5,4-b][1,4]thiazin-7-one The 6,7 dihydro-2-ethyl-8-methyl-3H-pyrimido[5,4-b][1,4]thiazine-4,7-dione of Example 115 (2.7g, 12.04 mmole) was suspended in approximately 150ml of phosphorus oxychloride and refluxed for about 20 hours. The solution was concentrated in vacuo and the excess phosphorus oxychloride was decomposed with the careful addition of ice and water. The aqueous solution was neutralized with the cautious addition of concentrated ammonium hydroxide, followed by the addition of sodium bicarbonate. The aqueous solution was extracted numerous times with chloroform; the extracts were combined, washed well with water, then brine, dried over magnesium sulfate, filtered and evaporated in vacuo to provide 2.4g (83%) of an off-white solid. The structural assignment was confirmed by infrared and nuclear magnetic resonance spectral analyses.

EXAMPLES 120–122

Utilizing the method of Example 119, the intermediates of Formula XV were chlorinated, providing the compounds of Formula XVI listed in TABLE VIII. These compounds were isolated as oils and required further purification utilizing flash chromatography, eluting with methylene chloride. The structural assignment of the compounds was confirmed by nuclear magnetic resonance spectral analysis.

TABLE VIII

| Example | Intermediate from Example | Intermediate of Formula XV and Compound of Formula XVI | | | Yield (%) | Spectral Analysis |
|---|---|---|---|---|---|---|
| | | $R_5$ | $R_7$ | B | | |
| 120 | 116 | $CH_2CH_3$ | $(CH_2)_3CH_3$ | $CH_2$ | 74 | NMR |
| 121 | 117 | $CH_2CH_3$ | $CH_2Ph$ | $CH_2$ | 43 | NMR |
| 122 | 118 | $CH_2CH_3$ | $CH_2Ph$ | $CHCH_2CH_3$ | 60 | NMR |

EXAMPLE 123

Step 13

Preparation of 6,7-Dihydro-2-ethyl-4-hydrazino-8-methyl-pyrimido[5,4-b][1,4]thiazin-7-one 4-Chloro-6,7-dihydro-2-ethyl-8-methylpyrimido[5,4-b][1,4]thiazin-7-one from Example 119 (2.4g, 9.93 mmole) was suspended in approximately 100ml of n-butanol. Hydrazine monohydrate (0.99g, 19.9 mmole) was added and the resultant mixture was refluxed for about 20 hours. The reaction mixture was allowed to cool and the precipitate was separated by filtration, washed with water and dried, providing 1.93g (81%) of 6,7-dihydro-2-ethyl-4-hydrazino-8-methylpyrimido[5,4-b}[1,4]thiazin-7-one. Infrared and nuclear magnetic resonance spectral analyses confirmed the structural assignment.

EXAMPLES 124-125

Using the procedure of Example 123, the intermediates of Formula XVI were reacted with hydrazine monohydrate to provide the respective intermediates of Formula XVII listed in TABLE IX. For Example 125, the reaction mixture was refluxed for about 3 hours instead of approximately 20 hours. The structures were confirmed by the indicated spectral analysis.

TABLE IX

| Example | Intermediate from Example | Intermediate of Formula XVI and Compound of Formula XVII | | | Yield (%) | Spectral Analysis |
|---|---|---|---|---|---|---|
| | | $R_5$ | $R_7$ | B | | |
| 124 | 120 | $CH_2CH_3$ | $(CH_2)_3CH_3$ | $CH_2$ | 93 | IR, NMR |
| 125 | 122 | $CH_2CH_3$ | $CH_2Ph$ | $CHCH_2CH_3$ | 85 | NMR |

EXAMPLE 126

Step 14

Preparation of 8,9-Dihydro-3,7-dimethyl-5-ethyl-1,2,4-triazolo[4,3-c]pyrimido[5,4-b][1,4]thiazin-8-one Approximately 20 ml of Triethyl orthoacetate was added to 1.1 g (4.6 mmole) of 6,7-dihydro-2-ethyl-4-hydrazino-8-methylpyrimido[5,4-b][1,4]thiazin-7-one (from Example 123) and the mixture heated at approximately 115° C. for about 20 hours. The reaction mixture was cooled in an ice bath; the precipitate was separated by filtration, washed with diethyl ether and dried, providing 0.65g (54%) of 8,9-dihydro-3,7-dimethyl-5-ethyl-1,2,4-triazolo[4,3-c]pyrimido[5,4 b][1,4]thiazin-8-one. Nuclear magnetic resonance spectral analysis confirmed the structural assignment.

EXAMPLES 127-130

Using the procedure of Example 126, the intermediates of Formula XVII were reacted with the indicated orthoester to provide the intermediates of Formula XVIII listed in TABLE X. The solid residues of Examples 128, 129 and 130 were triturated with hexanes, then separated by filtration, washed with diethyl ether and dried. The structural assignment of the compounds was confirmed by nuclear magnetic resonance spectral analysis.

TABLE X

| Example | Intermediate from Example | Orthoester | Compound of Formula XVIII | | | | Yield (%) |
|---|---|---|---|---|---|---|---|
| | | | $R_2$ | $R_5$ | $R_7$ | B | |
| 127 | 123 | triethyl orthopropionate | $CH_2CH_3$ | $CH_2CH_3$ | $CH_3$ | $CH_2$ | 63 |
| 128 | 124 | triethyl orthoacetate | $CH_3$ | $CH_2CH_3$ | $(CH_2)_3CH_3$ | $CH_2$ | 89 |
| 129 | 124 | triethyl orthopropionate | $CH_2CH_3$ | $CH_2CH_3$ | $(CH_2)_3CH_3$ | $CH_2$ | 67 |
| 130 | 125 | triethyl orthopropionate | $CH_2CH_3$ | $CH_2CH_3$ | $CH_2Ph$ | $CHCH_2CH_3$ | 56 |

EXAMPLE 131

Step 15

Preparation of 8,9-Dihydro-2,7-dimethyl-5-ethyl-1,2,4-triazolo[1,5-c]pyrimido[5,4-b][1,4]thiazin-8-one To approximately 20ml of methanol to which had been added 3-5 drops of a 25% solution of sodium methoxide in methanol was added 0.65g (2.5 mmole) of 8,9-dihydro-3,7-dimethyl-5-ethyl-1,2,4-triazolo[4,3-c]pyrimido[6,5-b][1,4]thiazin-8-one (from Example 126). The reaction mixture was refluxed for about 20 hours and allowed to cool. The precipitate was separated by filtration, washed with water and dried, providing 0.48g (74%) of 8,9-dihydro-2,7-dimethyl-5-ethyl-1,2,4-triazolo[1,5-c]pyrimido[5,4-b][1,4]thiazin-8-one, m.p. 187°-188° C. Analysis: Calculated for $C_{11}H_{13}N_5OS$: %C, 50.2; %H, 5.0; %N, 26.6; Found:

%C, 50.1; %H, 4.9; %N, 26.7. The structural assignment was confirmed by infrared and nuclear magnetic resonance spectral analyses.

EXAMPLES 132-135

Using the procedure of Example 131, the intermediates of Formula XVIII were rearranged to provide the compounds of Formula XIX, a subset of compounds of Formula I, listed in TABLE XI. For Examples 133 and 134, the reaction solution was concentrated in vacuo, and the resulting solid was purified by flash chromatography, eluting with 1:9 (by volume) ethyl acetate:-methylene chloride. For Example 135, after reflux for about 2 hours, the reaction solution was concentrated in vacuo and then purified by flash chromatography, eluting with methylene chloride. The structural assignment of the compounds was confirmed by infrared and nuclear magnetic resonance spectral analyses.

TABLE XI

| Example | Intermediate from Example | Product of Formula XIX |  |  |  | Calculated: % C; % H; % N<br>Found: % C; % H; % N<br>(m.p. in °C.) [% Yield] |
|---|---|---|---|---|---|---|
|  |  | $R_2$ | $R_5$ | $R_7$ | B |  |
| 132 | 127 | $CH_2CH_3$ | $CH_2CH_3$ | $CH_3$ | $CH_2$ | 52.0; 5.5; 25.3<br>51.8; 5.5; 25.5<br>(160-161) [86] |
| 133 | 128 | $CH_3$ | $CH_2CH_3$ | $(CH_2)_3CH_3$ | $CH_2$ | 55.1; 6.3; 22.9<br>54.9; 6.3; 22.9<br>(144-145) [52] |
| 134 | 129 | $CH_2CH_3$ | $CH_2CH_3$ | $(CH_2)_3CH_3$ | $CH_2$ | 56.4; 6.6; 21.9<br>56.1; 6.7; 22.1<br>(116-117.5) [61] |
| 135 | 130 | $CH_2CH_3$ | $CH_2CH_3$ | $CH_2Ph$ | $CHCH_2CH_3$ | 63.0; 6.1; 18.4<br>62.5; 6.1; 18.1<br>(94-95) [38] |

EXAMPLE 136

Step 16

Preparation of 6,7-Dihydro-2 methyl-4(3H)oxopyrimido[5,4-b][1,4]thiazine 5,6-Dihydro-3-ethoxy-2-ethoxycarbonyl 2H-[1,4]thiazine was prepared according to the procedure described in Great Britain Patent 2,143,234A and in Robert N. Henrie II et al, J. Med. Chem., 26, 559-563 (1983). Acetamidine hydrochloride (4.4g, 46.8 mmole) was suspended in approximately 80ml of ethanol to which was added 20.7g (95.8 mmole) of a 25% solution of sodium methoxide in methanol, followed by the addition of 9.4g (43.2 mmole) of 5,6-dihydro-3-ethoxy-2-ethoxycarbonyl-2H-[1,4]thiazine. The resultant mixture was refluxed for about 29 hours, allowed to cool and concentrated in vacuo to provide a brown solid residue. About 40ml of water were added to the residue; the suspension was cooled in an ice bath and carefully acidified (pH 5-6) with approximately 5ml of concentrated hydrochloric acid. The precipitate was separated by filtration, washed with water and dried in a vacuum oven at about 80° C. for approximately 20 hours, providing 6.7g (85%) of a light tan solid, 6,7-dihydro 2-methyl-4(3H)-oxopyrimido[5,4-b][1,4]thiazine. The structural assignment was confirmed by nuclear magnetic resonance spectral analysis.

EXAMPLE 137

Following the procedure of Example 136, with the exception that propionamidine acetate was used instead of acetamidine hydrochloride, 6,7-dihydro-2-ethyl-4(3H)-oxopyrimido[5,4-b][1,4]thiazine was isolated in 86% yield. The structural assignment was confirmed by nuclear magnetic resonance spectral analysis.

EXAMPLES 138-139

Step 17

Using the procedure of Step 12, Example 119, the intermediates of Formula XXI were chlorinated to provide the compounds of Formula XXII as listed in TABLE XII. For Example 138, filtration following the neutralization of the aqueous solution was necessary to remove a small amount of particulate matter; the product was isolated as a reasonably pure solid. The structural assignment of the compounds was confirmed by the indicated spectral analysis.

TABLE XII

| Example | Intermediate from Example | Intermediate of Formula XXI and Compound of Formula XXII |  |  | Yield (%) | Spectral Analysis |
|---|---|---|---|---|---|---|
|  |  | $R_5$ | $R_7$ | B |  |  |
| 138 | 136 | $CH_3$ | H | $CH_2$ | 72 | IR, NMR |
| 139 | 137 | $CH_2CH_3$ | H | $CH_2$ | 92 | NMR |

EXAMPLES 140-141

Step 18

Following the procedure of Step 13, Example 123, with the exception that hydrazine hydrate was used neat (about 3 ml/g) instead of hydrazine hydrate in n-butanol, the intermediates of Examples 138 and 139 were reacted to provide the intermediates of Formula XXIII as listed in TABLE XIII. The structures were confirmed by the indicated spectral analysis.

TABLE XIII

| Example | Intermediate from Example | Intermediate of Formula XXII and Compound of Formula XXIII |  |  | Yield (%) | Spectral Analysis |
|---|---|---|---|---|---|---|
|  |  | $R_5$ | $R_7$ | B |  |  |
| 140 | 138 | $CH_3$ | H | $CH_2$ | 87 | IR, NMR |
| 141 | 139 | $CH_2CH_3$ | H | $CH_2$ | 98 | NMR |

EXAMPLES 142-144

Step 19

Using the procedure of Step 14, Example 126, the intermediates of Formula XXIII were reacted with the designated orthoester to provide the compounds of Formula XXIV as listed in TABLE XIV. For Example 142, the reaction mixture was refluxed for about 3 days instead of approximately 20 hours. The structural assignment of the compounds was confirmed by nuclear magnetic resonance spectral analysis.

TABLE XIV

| Example | Intermediate from Example | Orthoester | Compound of Formula XXIV R$_2$ | R$_5$ | R$_7$ | B | Yield (%) |
|---|---|---|---|---|---|---|---|
| 142 | 140 | triethyl orthopropionate | CH$_2$CH$_3$ | CH$_3$ | H | CH$_2$ | 96 |
| 143 | 141 | triethyl orthoacetate | CH$_3$ | CH$_2$CH$_3$ | H | CH$_2$ | 88 |
| 144 | 141 | triethyl orthopropionate | CH$_2$CH$_3$ | CH$_2$CH$_3$ | H | CH$_2$ | 90 |

EXAMPLES 145–147

Step 20

Following the procedure of Step 15, Example 131, the intermediates of Formula XXIV were rearranged to provide the compounds of Formula XXV as listed in TABLE XV. For each of the compounds, the reaction mixture was refluxed for about 5-6 hours, about 4 hours and about 20 hours respectively, then concentrated in vacuo. The residue was suspended in water (approximately 10ml/g of starting material) and extracted five times with 60ml portions of chloroform. The combined extracts were washed with about 50ml of water, then approximately 75ml of brine, dried over magnesium sulfate, filtered, and concentrated in vacuo to provide a solid which was triturated with hexanes, filtered and dried, yielding a solid which was recrystallized from benzene:hexanes. The structural assignment of the compounds of Formula XXV, a subset of the compounds of Formula I, was confirmed by infrared and nuclear magnetic resonance spectral analyses.

TABLE XV

| Example | Intermediate from Example | Product of Formula XXV R$_2$ | R$_5$ | R$_7$ | B | Calculated: % C; % H; % N Found: % C; % H; % N (m.p. in °C.) [% yield] |
|---|---|---|---|---|---|---|
| 145 | 142 | CH$_2$CH$_3$ | CH$_3$ | H | CH$_2$ | 49.2; 5.8; 28.7<br>48.8; 5.8; 29.0<br>(139–143) [92] |
| 146 | 143 | CH$_3$ | CH$_2$CH$_3$ | H | CH$_2$ | 51.0; 5.6; 29.8<br>50.8; 5.6; 29.8<br>(139–141) [93] |
| 147 | 144 | CH$_2$CH$_3$ | CH$_2$CH$_3$ | H | CH$_2$ | 53.0; 6.1; 28.1<br>53.0; 6.0; 28.2<br>(104–107) [62] |

EXAMPLE 148

Preparation of 2,5-diethyl-10-oxo-1,2,4-triazolo[1,5-c]pyrimido[5,4-b][1,4]thiazine The sulfoxide of the compound of Example 147 was prepared by dissolving 0.5g (2 mmole) of 2,5-diethyl-1,2,4-triazolo[1,5-c]pyrimido[5,4-b][1,4]thiazine in a mixture of approximately 25ml of ethyl alcohol and about 5ml of water. To this solution was added 1.0g (4.7 mmole) of sodium metaperiodate and the resultant solution was stirred at about 20° C. for approximately 2 hours, at which time thin layer chromotographic analysis, eluting with ethyl acetate indicated the absence of starting material. The reaction solution was then diluted with about 150ml of water and extracted thrice with approximately 75ml of chloroform. The chloroform extracts were combined, dried over magnesium sulfate, filtered and concentrated in vacuo to provide a solid in about 87% yield, m.p. 217°-219° C. The crude solid was recrystallized from ethyl acetate to provide 0.25g of 2,5-diethyl-10-oxo-1,2,4-triazolo[1,5-c]pyrimido[5,4-b][1,4]thiazine, m.p. 217-219° C. Analysis: Calculated for C$_{11}$H$_{15}$N$_5$SO: %C, 49.8; %H, 5.7; %N, 26.4; Found: %C, 49.8; %H, 5.8; %N, 26.9. The structural assignment was confirmed by infrared and nuclear magnetic resonance spectral analyses.

EXAMPLE 149

Step 21

Preparation of 8.9-dihydro-5,7-dimethyl-2-ethyl-1,2,4-triazolo[1,5-c]pyrimido[5,4-b][1,4]thiazine The 8,9-dihydro-2-ethyl 5-methyl-1,2,4-triazolo[1,5-c]pyrimido[5,4-b][1,4]thiazine of Example 145 (1.0g, 4.3 mmole) was dissolved in approximately 25ml of dry N,N-dimethylformamide and the mixture was stirred under a nitrogen atmosphere at about 20° C. during the addition of 0.2g (5.0 mmole) of a 60% oil dispersion of sodium hydride; a yellow solid formed and gas evolution was observed. After addition was complete, the mixture was allowed to stir for about 20 minutes at which time the solid had dissolved. Methyl iodide (1.2g, 8.5 mmole) was then added with continued stirring under a nitrogen atmosphere at about 20° C. When addition was complete, the solution was allowed to stir at approximately 20° C. for about 5 hours. The reaction solution was then poured into about 40ml of water and extracted five times with 40ml portions of chloroform; the combined extracts were washed six times with 200ml portions of water, dried over magnesium sulfate, filtered and concentrated in vacuo to provide a tan oil. The oil was purified by flash chromatography, eluting with 1:4 (by volume) ethyl acetate:methylene chloride, yielding 0.8g (76%) of a pale yellow solid which on recrystallization from cyclohexane provided 0.6g of 8,9-dihydro-5,7-dimethyl-2-ethyl-1,2,4-triazolo[1,5-c]pyrimido[5,4-b][1,4]thiazine, m.p. 103°-104° C. Analysis: Calculated for C$_{11}$H$_{15}$N$_5$S: %C, 53.0; %H, 6.1; %N, 28.1; Found: %C, 52.6; %H, 6.0; %N, 28.4. The structural assignment was confirmed by infrared and nuclear magnetic resonance spectral analyses.

EXAMPLES 150-156

Following the procedure of Example 149, the designated compounds of Formula XXV were reacted with an alkyl halide to form the compounds of Formula XXVI, a subset of the compounds of Formula I, as listed in TABLE XVI. For Example 150, after the addition of the alkyl halide, the reaction mixture was refluxed about 2 hours instead of stirring for approximately 5 hours at about 20° C. For all other examples, the reaction mixture was stirred at approximately 20° C. for about 20 hours before work-up. The structural assignment of the compounds of Formula XXVI was confirmed by infrared and nuclear magnetic resonance spectral analyses.

dioxo-2-methyl-1,2,4-triazolo[1,5-c]pyrimido[5,4-b][1,4]thiazine as a white crystalline solid, m.p. 218°-221° C. Analysis: Calculated for $C_{12}H_{17}N_5SO$: %C, 48.8; %H, 5.8; %N, 23.7; Found: %C, 48.8; %H, 5.8; %N, 23.8. The structural assignment was confirmed by infrared spectral analysis.

EXAMPLE 158

Preparation of 8,9-dihydro-2,5,7-triethyl-1,2,4-triazolo[1,5-c]pyrimido[5,4-b][1,4]thiazine dihydrogen sulfate The dihydrogen sulfate salt of the compound of Example 154 was prepared by dissolving 0.5g (1.8 mmole) of 8,9-dihydro-2,5,7-triethyl-1,2,4-triazolo[1,5-c]pyrimido[5,4-b][1,4]thiazine in approximately 5ml of ethyl alcohol. To this solution, was added dropwise 0.18g (1.8mmole) of concentrated sulfuric acid and the

TABLE XVI

| Example | Intermediate from Example | Alkyl Halide | Product of Formula XXVI | | | Flash Chromatography Solvent System [Recrystallization Solvent] | Calculated: % C; % H; % N Found: % C; % H; % N (m.p. in °C.) [% yield] |
|---|---|---|---|---|---|---|---|
| | | | $R_2$ | $R_5$ | $R_7$ | | |
| 150 | 145 | $CH_3CH_2I$ | $CH_2CH_3$ | $CH_3$ | $CH_2CH_3$ | 1:4 EtOAc:$CH_2Cl_2$ [Cyclohexane] | 54.7; 6.5; 26.6 54.6; 6.6; 26.8 (91-92) [55] |
| 151 | 146 | $CH_3I$ | $CH_3$ | $CH_2CH_3$ | $CH_3$ | 1:9 EtOAc:$CH_2Cl_2$ then 1:4 EtOAc:$CH_2Cl_2$ [not recrystallized] | 53.0; 6.1; 28.1 52.6; 6.1; 28.1 (159-160) [43] |
| 152 | 147 | $CH_3I$ | $CH_2CH_3$ | $CH_2CH_3$ | $CH_3$ | (not chromatographed) [Petroleum Ether] | 54.7; 6.5; 26.6 55.0; 6.5; 26.9 (75-77) [6] |
| 153 | 146 | $CH_3CH_2I$ | $CH_3$ | $CH_2CH_3$ | $CH_2CH_3$ | 1:9 EtOAc:$CH_2Cl_2$ [not recrystallized] | 54.7; 6.5; 26.6 54.7; 6.5; 26.6 (92-93) [21] |
| 154 | 147 | $CH_3CH_2I$ | $CH_2CH_3$ | $CH_2CH_3$ | $CH_2CH_3$ | 1:9 EtOAc:$CH_2Cl_2$ [Petroleum Ether] | 56.3; 6.9; 25.2 56.0; 6.8; 25.2 (75-76) [30] |
| 155 | 146 | $PhCH_2Cl$ | $CH_3$ | $CH_2CH_3$ | $CH_2Ph$ | 1:9 EtOAc:$CH_2Cl_2$ [not recrystallized] | 62.7; 5.9; 21.5 62.5; 5.9; 21.6 (83-85) [36] |
| 156 | 147 | $PhCH_2Cl$ | $CH_2CH_3$ | $CH_2CH_3$ | $CH_2Ph$ | (not chromatographed) [Petroleum Ether] | 63.7; 6.2; 20.6 63.7; 6.2; 20.9 (68-70) [38] |

EXAMPLE 157

Preparation of 5,7-diethyl-10,10-dioxo-2-methyl-1,2,4-triazolo[1,5-c]pyrimido[5,4-b][1,4]thiazine The sulfone of the compound of Example 153 was prepared by dissolving 2.0g (7.6 mmole) of 5,7-diethyl-2-methyl-1,2,4-triazolo[1,5-c]pyrimido[5,4-b][1,4]thiazine in about 36ml of chloroform and cooling the resultant solution to approximately 0° C. in an ice bath. To this solution was added, in small portions, a suspension of 4.0g (18.5 mmole) of meta-chloroperbenzoic acid (80–85% pure) in about 35ml of chloroform. When addition was complete, the solution was stirred at about 0° C. for approximately 2 hours, at which time thin layer chromatographic analysis, eluting with ethyl acetate indicated the absence of starting material. The reaction solution was diluted with about 1 liter of chloroform and washed sequentially with 5% sodium hydroxide solution (thrice with about 500ml) and then with water (thrice with 500ml). The chloroform solution was dried over magnesium sulfate, filtered and concentrated in vacuo to provide 2.48g of the light pink solid. The crude solid was purified by flash chromatography, eluting with ethyl acetate. The fractions containing the pure compound were combined and concentrated in vacuo. The solid obtained was triturated with hexanes, filtered and dried to provide 0.5g of 5,7-diethyl-10,10-resultant solution was diluted with diethyl ether to produce a slightly cloudy solution. Upon standing at about 20° C., a solid precipitated. The solid was separated by suction filtration and dried in a vacuum oven (without heat) to provide 0.6g (89%) of 8,9-dihydro-2,5,7-triethyl-1,2,4-triazolo[1,5-c]pyrimido[5,4-b][1,4]thiazine dihydrogen sulfate, m.p. 226°-229° C. Analysis: Calculated for $C_{13}H_{19}N_5S.H_2SO_4$: %C, 41.6; %H, 5.6; %N, 18.7; Found: %C, 41.8; %H, 5.7; %N, 18.4.

EXAMPLE 159

Preparation of 7-acetyl-8,9-dihydro-2-ethyl-5-methyl-1,2,4-triazolo[1,5-c]pyrimido[5,4-b][1,4]thiazine To a solution of 0.9g (3.62 mmole) of 8,9-dihydro-2-ethyl-5-methyl-1,2,4-triazolo[1,5-c]pyrimido[5,4-b][1,4]thiazine (from Example 145) in approximately 50ml of chloroform was added 0.4g (4.05 mmole) of triethylamine, followed by the addition of 0.58g (7.4 mmole) of acetyl chloride. The reaction mixture was refluxed under a nitrogen atmosphere for about 2 hours at which time thin layer chromatographic analysis, eluting with ethyl acetate, indicated that the reaction was complete. After cooling and dilution with about 100ml of chloroform, the reaction solution was washed twice with 50ml portions of water, twice with 40ml portions of a 5% solution of hydrochloric acid, twice with 50ml portions of aqueous sodium bicarbonate solution, twice with 50ml portions of water, dried over magnesium sulfate, filtered and concentrated in vacuo to provide a yellow solid. The solid was flash chromatographed, eluting with ethyl acetate, to provide 0.5g (23%) of product which after recrystallization from benzene:hexanes yielded 0.32g of a white solid, 7-acetyl-8,9-dihydro-2-ethyl-5-methyl-1,2,4-triazolo[1,5 c]pyrimido[5,4-b][1,4]thiazine, m.p. 164°–165° C. Analysis: Calculated for $C_{12}H_{15}N_5SO$: %C, 52.0; %H, 5.5; %N, 25.3; Found: %C, 52.1; %H, 5.5; %N, 25.4. The structural assignment was confirmed by infrared and nuclear magnetic resonance spectral analyses.

EXAMPLES 160 and 161

Using the procedure of Example 159, the designated compounds of Formula XXV were reacted with acetyl chloride to provide the compounds of Formula XXVI, a subset of the compounds of Formula I, as listed in TABLE XVII. For Example 160, after refluxing for about 2 hours, the reaction mixture was stirred at approximately 20° C. for about 20 hours before work-up.

TABLE XVII

| Example | Intermediate from Example | Product of Formula XXVI $R_2$ | $R_5$ | $R_7$ | Flash Chromatography Elution Solvent System | Calculated: % C; % H; % N Found: % C; % H; % N (m.p. in °C.) [% yield] |
|---|---|---|---|---|---|---|
| 160 | 146 | $CH_3$ | $CH_2CH_3$ | O‖CCH$_3$ | 1:9 EtOAc:CH$_2$Cl$_2$ then 1:4 EtOAc:CH$_2$Cl$_2$ then 1:1 EtOAc:CH$_2$Cl$_2$ | 52.0; 5.4; 25.2 52.8; 5.6; 25.2 (189–191) [60] |
| 161 | 147 | $CH_2CH_3$ | $CH_2CH_3$ | O‖CCH$_3$ | 1:9 EtOAc:CH$_2$Cl$_2$ | 53.6; 5.9; 24.0 53.6 5.8; 24.3 (148–150) [76] |

EXAMPLES 162–163

Using the method of Example 102 the indicated intermediates were reduced to provide intermediates of Formula X as shown in the following Table.

TABLE XVIII

| | | Compound of Formula X | |
|---|---|---|---|
| Example | Intermediate | $R_5$ | $R_{10}$ |
| 162 | Example 81 | $CH_2CH_3$ | $CH_3$ |
| 163 | Example 84 | $CH_3$ | $CH_3$ |

EXAMPLES 164–168

Using the method of Example 87 except no solvent was used, the indicated intermediates were reacted to provide intermediates of Formula IV as shown in the following Table.

TABLE XIX

| | | Compound of Formula IV | |
|---|---|---|---|
| Example | Intermediate | $R_5$ | $R_{10}$ |
| 164 | Example 163 | $CH_3$ | $CH_3$ |
| 165 | Example 162 | $CH_2CH_3$ | $CH_3$ |
| 166 | Example 174 | $CH_2CH_3$ | $CH_2CH_3$ |
| 167 | Example 173 | $CH_3$ | $CH_2Ph$ |
| 168 | Example 172 | $CH_3$ | $CH_2CH_3$ |

EXAMPLES 169–170

Step 7

The method of Melik-Ogandzhanyan, et al., Khimiya Geterotsiklicheskikh Soedinenii, 1985, 974 was used to prepare 4-chloro-6,7-dihydro-2-methyl-5H-pyrimido[4,5-b][1,4]oxazin-6-one and 4-chloro 6,7-dihydro-2 ethyl-5H-pyrimido[4,5 b][1,4]oxazin-6-one which were reacted separately with borane-methyl sulfide complex using the method of Example 102 to provide intermediates of Formula IX wherein $Q_1$ is O, $Q_2$ is NH and B is methylene as shown in the following Table.

TABLE XX

| Example | Compound of Formula IX $R_5$ |
|---|---|
| 169 | $CH_3$ |
| 170 | $CH_2CH_3$ |

EXAMPLE 171–174

Step 8

Using the method of Example 81, the indicated intermediates were reacted to provide intermediates of Formula X as shown in the following Table.

TABLE XXI

| | | Compound of Formula X | |
|---|---|---|---|
| Example | Intermediate | $R_5$ | $R_{10}$ |
| 171 | Example 169 | $CH_3$ | $CH_3$ |
| 172 | Example 169 | $CH_3$ | $CH_2CH_3$ |
| 173 | Example 169 | $CH_3$ | $CH_2Ph$ |
| 174 | Example 170 | $CH_2CH_3$ | $CH_2CH_3$ |

What is claimed is:

1. A compound of the formula

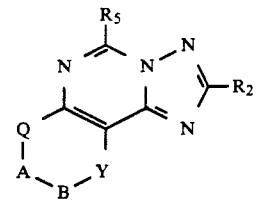

wherein A is methylene or carbonyl; B is methylene, carbonyl or —$CHR_9$—; Q is N-$r_7$ or O, with the proviso that when Q is O then A is methylene and B is methylene or carbonyl; Y is N-$R_{10}$, or O, with the provisos that when Y is N-$R_{10}$, Q is O, when Q is $NR_7$, Y is O and B is methylene or —$CHR_9$—, and when Q is O, Y is N-$R_{10}$; $R_2$ is hydrogen or lower alkyl; $R_5$ is lower alkyl; $R_7$ is hydrogen, lower alkyl, benzyl or acetyl, $R_9$ is lower alkyl; $R_{10}$ is lower alkyl or benzyl; or a pharmaceutically acceptable acid-addition salt of said compound wherein A is methylene and B is methylene or —$CHR_9$—.

2. A compound according to claim 1, wherein Y is O.

3. A compound according to claim 2, wherein A is methylene.

4. A compound according to claim 2, wherein A is carbonyl.

5. A compound according to claim 2, selected from the group of
8,9-dihydro-2-ethyl-5-methyl-7H-1,2,4-triazolo[1,5-c]pyrimido[5,4-b][1,4]oxazin-8-one,
8,9dihydro-2,5,7-triethyl-1,2,4-triazolo[1,5-c]pyrimido[5,4-b][1,4]oxazin-8-one hydrate,
8,9-dihydro-2-ethyl-5-methyl-7H-1,2,4-triazolo[1,5-c]pyrimido[5,4b][1,4]oxazine,
2,5-diethyl-8,9-dihydro-7H-1,2,4-triazolo[1,5-c]pyrimido[5,4b][1,4]oxazin-8-one,
2,9-diethyl-8,9-dihydro-7H-5-methyl-1,2,4-triazolo[1,5-c]pyrimido[5,4-b][1,4 oxazin-8-one,
8,9-dihydro-5,9-dimethyl-2-ethyl-7H-1,2,4-triazolo[1,5-c]pyrimido[5,4-b][1,4]oxazin-8-one,
8,9-dihydro-2,5,9-trimethyl-7H-1,2,4-triazolo[1,5-c]pyrimido[5,4-b][1,4]oxazin-8-one,
8,9-dihydro-2,5,9-triethyl-7H-1,2,4-triazolo[1,5-c]pyrimido-[5,4-b][1,4]oxazin-8-one,
5,9-diethyl-8,9-dihydro-2-methyl-7H-1,2,4-triazolo[1,5-c]pyrimido[5,4-b][1,4]oxazin-8-one, and
2,5-diethyl-8,9-dihydro-9-methyl-7H-1,2,4-triazolo[1,5-c]pyrimido[5,4-b][1,4]oxazin-8-one.

6. A compound of the formula

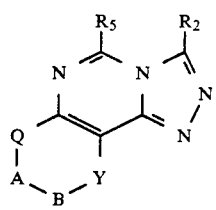

wherein A is methylene or carbonyl; B is methylene, carbonyl or —CHR$_9$—; Q is N-R$_7$ or O, with the proviso that when Q is O, then A is methylene and B is methylene or carbonyl; Y is N-R$_{10}$ or O, with the provisos that when Y is N-R$_{10}$, Q is O, when Q is NR$_7$, Y is O and B is methylene or —CHR$_9$—, and when Q is O, Y is N-R$_{10}$; R$_2$ is hydrogen or lower alkyl; R$_5$ is lower alkyl; R$_7$ is hydrogen, lower alkyl, benzyl or acetyl; R$_9$ is lower alkyl; and R$_{10}$ is lower alkyl or benzyl.

7. A compound according to claim 6, wherein Y is O.

8. A compound according to claim 7, wherein A is methylene.

9. A compound according to claim 7, wherein A is carbonyl.

10. A method for obtaining bronchodilation in a mammal, comprising administering a bronchodilator compound to said mammal, said bronchodilator compound being of the formula

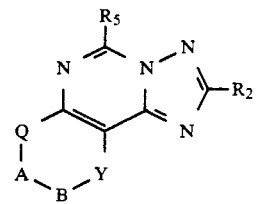

wherein A is methylene or carbonyl; B is methylene, carbonyl or —CHR$_9$—; Q is N-R$_7$ or O, with the proviso that when Q is O then A is methylene and B is methylene or carbonyl; Y is N-R$_{10}$, or O, with the provisos that when Y is N-R$_{10}$, Q is O, when Q is N-R$_7$, Y is O and B is methylene or —CHR$_9$—, and when Q is O, Y is N-R$_{10}$; R$_2$ is hydrogen or lower alkyl; R$_5$ is lower alkyl; R$_7$ is hydrogen, lower alkyl, benzyl or acetyl, and R$_{10}$ is lower alkyl or benzyl; or a pharmaceutically acceptable salt of said compound wherein A is methylene and B is methylene or —CHR$_9$—, said compound being administered to said mammal in an amount sufficient to provide bronchodilation.

11. A method according to claim 10, wherein Y is O.

12. A method according to claim 11, wherein A is methylene.

13. A method according to claim 11, wherein A is carbonyl.

14. A method according to claim 11, wherein said compound is administered orally.

15. A compound according to claim 1 wherein Q is O and Y is N-R$_{10}$.

16. A compound according to claim 6 wherein Q is O and Y is N-R$_{10}$.

17. A compound according to claim 6 wherein Q is O and Y is N-R$_{10}$.

18. A method according to claim 10 wherein Q is O and Y is N-R$_{10}$.

19. A compound according to claim 16 selected from the group consisting of 2,5-diethyl-8,9-dihydro-10-methyl-1,2,4-triazolo[1,5-c]pyrimido[4,5-b][1,4]oxazine and 8,9-dihydro-2,5,10-triethyl-1,2,4-triazolo[1,5-c]pyrimido[4,5-b][4,5]oxazine.

* * * * *

UNITED STATES PATENT AND TRADEMARK OFFICE
CERTIFICATE OF CORRECTION

PATENT NO. : 5,089,493
DATED : February 18, 1992
INVENTOR(S) : James J. Wade It is certified that error appears in the above-identified patent and that said Letters Patent is hereby corrected as shown below:

Col. 18, Example 64, under Column $R_{10}$, "$CH_2$" should read --$CH_3$--.

Col. 36, line 45, "claim 16" should read --claim 15--.

Signed and Sealed this

Fourteenth Day of September, 1993

Attest:

BRUCE LEHMAN

*Attesting Officer*  *Commissioner of Patents and Trademarks*